(12) United States Patent
Busacca et al.

(10) Patent No.: US 7,514,557 B2
(45) Date of Patent: Apr. 7, 2009

(54) PROCESS FOR PREPARING ACYCLIC HCV PROTEASE INHIBITORS

(75) Inventors: Carl Alan Busacca, Poughkeepsie, NY (US); Rogelio Perez Frutos, Sandy Hook, CT (US); Nizar Haddad, Danbury, CT (US); Suresh R. Kapadia, Danbury, CT (US); Jon Charles Lorenz, New Milford, CT (US); Anjan Saha, Hamden, CT (US); Chris Hugh Senanayake, Brookfield, CT (US); Xudong Wei, Ridgefield, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 570 days.

(21) Appl. No.: 11/135,533

(22) Filed: May 23, 2005

(65) Prior Publication Data

US 2005/0267151 A1    Dec. 1, 2005

Related U.S. Application Data

(60) Provisional application No. 60/574,182, filed on May 25, 2004, provisional application No. 06/652,018, filed on Feb. 11, 2005, provisional application No. 60/660,745, filed on Mar. 11, 2005.

(51) Int. Cl.
*C07D 215/38* (2006.01)
*A61K 31/44* (2006.01)

(52) U.S. Cl. .................. 546/154; 546/153; 514/312; 514/18

(58) Field of Classification Search ................ 546/153, 546/154; 514/18, 312
See application file for complete search history.

(56) References Cited

U.S. PATENT DOCUMENTS

| | | |
|---|---|---|
| 6,323,180 B1 | 11/2001 | Llinas-Brunet et al. |
| 6,608,027 B1 | 8/2003 | Tsantrizos et al. |
| 6,867,185 B2 | 3/2005 | Campbell et al. |
| 6,878,722 B2 | 4/2005 | Campbell et al. |
| 2003/0224977 A1 | 12/2003 | Llinas-Brunet et al. |
| 2004/0248779 A1 | 12/2004 | Dersch et al. |
| 2005/0020503 A1* | 1/2005 | Llinas-Brunet et al. ....... 514/18 |
| 2005/0049187 A1 | 3/2005 | Brandenburg et al. |
| 2005/0075279 A1 | 4/2005 | Llinas-Brunet et al. |
| 2005/0080005 A1 | 4/2005 | Llinas-Brunet et al. |
| 2005/0209135 A1 | 9/2005 | Busacca et al. |
| 2006/0205638 A1 | 9/2006 | Busacca et al. |
| 2008/0177029 A1 | 7/2008 | Busacca et al. |

FOREIGN PATENT DOCUMENTS

| | | |
|---|---|---|
| WO | 0009558 A1 | 2/2000 |
| WO | WO 00/09543 A2 | 2/2000 |
| WO | 03053349 A2 | 7/2003 |
| WO | 03099274 A1 | 12/2003 |
| WO | 2004037855 A1 | 5/2004 |
| WO | 2004092203 A2 | 10/2004 |
| WO | WO 2004/103996 A1 | 12/2004 |
| WO | WO 2005/028501 A1 | 3/2005 |

OTHER PUBLICATIONS

Smith, E. M. et al, "Synthesis and Pharmacological Activity of Angiotensin Converting Enzyme Inhibitors: N-(Mercaptoacyl)-4-substituted-(S)-prolines", J. Med. Chem., 1988, 31, pp. 875-885.
Perrone, R., "2-(Aryloxy)Ethylamine Derivatives: Ring Opened Congeners Of Long Chain 1-Arylpiperazines With High 5-HT1A Receptor Affinity and Selectivity Versus D2 and alpha 1 Receptors", Med. Chem. Res 9:5 (1999) pp. 340-353.
Wrobel; Silane-Mediated Direct Condensation of Nitroarenes with Cinnamyl-type Sulfones. The way to 2-Aryl-4-X-quinolines and Their Hetero Analogs; Tetrahedron; vol. 54; 1998; pp. 2607-2618.

* cited by examiner

*Primary Examiner*—D. Margaret Seaman
(74) *Attorney, Agent, or Firm*—Michael P. Morris; Mary-Ellen M. Devlin; Philip I. Datlow

(57) ABSTRACT

Disclosed are highly convergent processes for preparing compounds of formula (I), which compounds are potent active agents for the treatment of hepatitis C virus (HCV) infection:

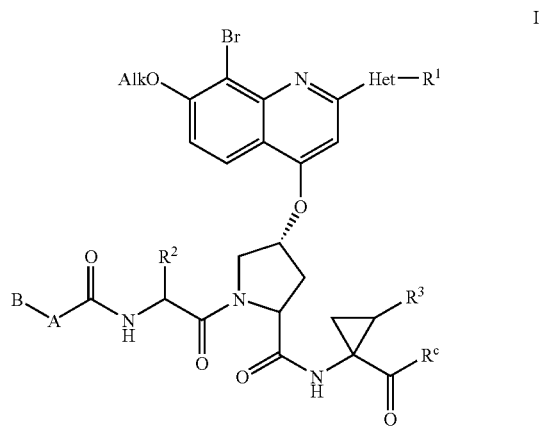

The disclosed processes use $S_N$Ar-type coupling reactions between peptidic compounds having a hydroxyproline moiety of the following formula:

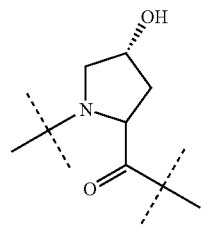

and halogenated or sulfonated bromoquinoline compounds.

12 Claims, No Drawings

PROCESS FOR PREPARING ACYCLIC HCV PROTEASE INHIBITORS

CROSS-REFERENCE TO RELATED APPLICATIONS

This application claims the benefit of the following U.S. Provisional Applications: 60/574,182, filed May 25, 2004; 60/652,018, filed Feb. 11, 2005 and 60/660,745, filed Mar. 11, 2005.

BACKGROUND OF THE INVENTION

1. Technical Field

The invention relates to an improved process for the preparation of acyclic compounds useful as agents for the treatment of hepatitis C viral (HCV) infections.

2. Background Information

The compounds of the following formula (I) and methods for their preparation are disclosed in the following patent publications: WO 00/09543; U.S. Pat. No. 6,323,180 B1; and U.S. Patent Application Publication No. 2005/0020503 A1:

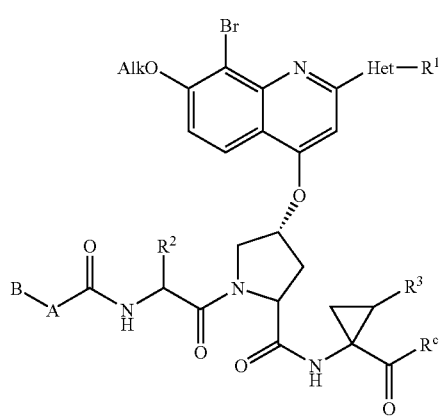

wherein Het is a five-, six- or seven-membered saturated or unsaturated heterocycle containing from one to four heteroatoms selected from nitrogen, oxygen and sulfur; said heterocycle being substituted with $R^1$ at any available position on the heterocycle;

$R^1$ is $R^{20}$, —$NR^{22}COR^{20}$, —$NR^{22}COOR^{20}$—$NR^{22}R^{21}$ and —$NR^{22}CONR^{21}R^{23}$, wherein $R^{20}$ is selected from $(C_{1-8})$alkyl, $(C_{3-7})$cycloalkyl and $(C_{3-7})$cycloalkyl$(C_{1-4})$alkyl-, wherein said cycloalkyl or cycloalkylalkyl may be mono-, di- or tri-substituted with $(C_{1-3})$alkyl;

$R^{21}$ is H or has one of the meanings of $R^{20}$ as defined above, $R^{22}$ and $R^{23}$ are independently selected from H and methyl, Alk is a $C_1$-$C_6$ alkyl group;

A is O or NH;

B is $(C_{1-10})$alkyl, $(C_{3-7})$cycloalkyl, $(C_{3-7})$cycloalkyl$(C_{1-4})$alkyl,
  a) wherein said cycloalkyl, cycloalkylalkyl may be mono-, di- or tri-substituted with $(C_{1-3})$alkyl; and
  b) wherein said alkyl, cycloalkyl, cycloalkylalkyl may be mono- or di-substituted with substituents selected from hydroxy and $(C_{1-4})$alkoxy; and
  c) wherein all said alkyl-groups may be mono-, di- or tri-substituted with halogen; and
  d) wherein said cycloalkyl-groups being 4-, 5-, 6- or 7-membered having optionally one (for the 4-, 5, 6, or 7-membered) or two (for the 5-, 6- or 7-membered) —$CH_2$-groups not directly linked to each other replaced by —O— such that the O-atom is linked to the group A via at least two C-atoms;

$R^2$ is $(C_{1-8})$alkyl, $(C_{3-7})$cycloalkyl or $(C_{3-7})$cycloalkyl $(C_{1-3})$ alkyl, wherein said cycloalkyl groups may be mono-, di- or tri-substituted with $(C_{1-4})$alkyl;

$R^3$ is ethyl or vinyl;

$R^C$ is hydroxyl, $C_1$-$C_6$ alkoxy or $NHSO_2R^S$ wherein $R^S$ is $(C_{1-6})$alkyl, $(C_{3-7})$cycloalkyl, $(C_{3-7})$cycloalkyl$(C_{1-6})$alkyl, phenyl, naphthyl, pyridinyl, phenyl$(C_{1-4})$alkyl, naphthyl $(C_{1-4})$alkyl or pyridinyl$(C_{1-4})$alkyl; all of which optionally being mono-, di- or tri-substituted with substituents selected from halogen, hydroxy, cyano, $(C_{1-4})$alkyl, $(C_{1-6})$ alkoxy, —CO—$NH_2$, —CO—NH($C_{1-4}$-alkyl), —CO—N $(C_{1-4}$-alkyl$)_2$, —$NH_2$, —NH($C_{1-4}$-alkyl) and —N($C_{1-4}$-alkyl$)_2$; and all of which optionally being monosubstituted with nitro;

or $R^S$ can be further selected from: —NH($C_{1-6}$alkyl), N($C_{1-6}$alkyl$)_2$, -Het,

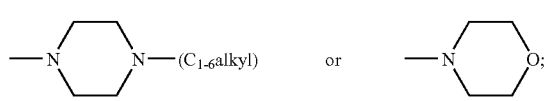

or a pharmaceutically acceptable salt or ester thereof.

The compounds of formula (I) are disclosed in the above-mentioned patent documents as being active agents for the treatment of hepatitis C virus (HCV) infections. The methods disclosed for the preparation of these compounds included many synthetic steps and were extremely linear, in that groups were built up sequentially in small increments, rather than synthesizing large fragments and bringing them together (convergency). The problem addressed by the present invention is to provide highly convergent processes which allow for the manufacture of these compounds with a minimum number of steps and with sufficient overall yield.

BRIEF SUMMARY OF THE INVENTION

The processes provided by the present invention, as described herein, are highly convergent and this convergency manifests itself in a much shorter synthetic sequence leading to the compounds of Formula (I). The $S_NAr$ assembly strategy of the present invention utilizing monopeptides, dipeptides and tripeptides eliminates steps from the known synthetic sequence since it is not necessary to invert the natural hydroxyproline stereochemistry. This allows one to utilize the far less expensive natural aminoacid as starting material, thereby gaining a further economic advantage.

The processes of the present invention also provide for the preparation of certain intermediates in crystalline form. This crystallinity imparts numerous large scale handling and storage advantages over an amorphous solid or an oil.

The processes of the present invention all provide for the preparation of Formula (I) via $S_NAr$ coupling reaction between a compound having a hydroxyproline moiety of the following general formula A:

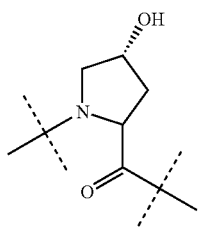

A and the following quinoline compound QUIN:

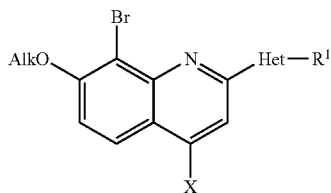

QUIN wherein Het and $R^1$ are as defined previously and X is a halogen atom or an $SO_2R$ group, wherein R is $C_{1-6}$alkyl, $C_6$ or $C_{10}$ aryl or heteroaryl, leading to compounds of the following general formula B:

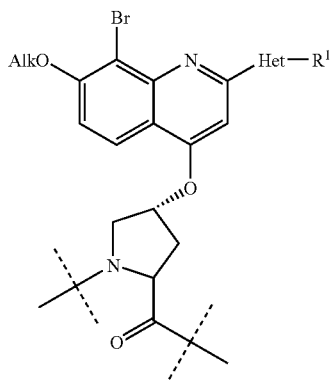

B

Depending upon the hydroxyproline compound of general formula A that is used in this step, be it a mono-, di- or tripeptide, highly convergent processes leading to compound of Formula (I) are possible by employing standard peptide coupling techniques as described in the schemes set forth herein.

The present invention is therefore directed to a multi-step synthetic process for preparing compounds of formula (I) using the synthetic sequences as described herein; particular individual steps of this multi-step process; and particular individual intermediates used in this multi-step process.

The present invention is also directed to novel crystalline forms of particular intermediates and also of the compound of Formula (I).

DETAILED DESCRIPTION OF THE INVENTION

Definition of Terms and Conventions Used

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $(C_{1-8})$alkyl means an alkyl group or radical having 1 to 8 carbon atoms and $(C_{3-7})$cycloalkyl means a cycloalkyl group having from 3 to 7 carbon atoms in the ring. In general, for groups comprising two or more subgroups, the last named group is the radical attachment point, for example, "cycloalkylalkyl" means a monovalent radical of the formula cycloalkyl-alkyl- and phenylalkyl means a monovalent radical of the formula phenyl-alkyl-. Unless otherwise specified below, conventional definitions of terms control and conventional stable atom valences are presumed and achieved in all formulas and groups.

The term "alkyl" as used herein, either alone or in combination with another substituent, means acyclic, straight or branched chain alkyl substituents containing the specified number of carbon atoms.

The term "alkoxy" as used herein, either alone or in combination with another substituent, means an alkyl group as defined above linked as a substituent through an oxygen atom: alkyl-O—.

The term "$C_6$ or $C_{10}$ aryl" as used herein, either alone or in combination with another substituent, means either an aromatic monocyclic system containing 6 carbon atoms or an aromatic bicyclic system containing 10 carbon atoms. For example, aryl includes a phenyl or a naphthyl ring system.

The term "Het" as used herein, either alone or in combination with another substituent, means a monovalent substituent derived by removal of a hydrogen from a five-, six-, or seven-membered saturated or unsaturated (including aromatic) heterocycle containing carbon atoms and from one to four ring heteroatoms selected from nitrogen, oxygen and sulfur. Examples of suitable heterocycles include: tetrahydrofuran, thiophene, diazepine, isoxazole, piperidine, dioxane, morpholine, pyrimidine or

The term "Het" also includes a heterocycle as defined above fused to one or more other cycle be it a heterocycle or a carbocycle, each of which may be saturated or unsaturated. One such example includes thiazolo[4,5-b]-pyridine. Although generally covered under the term "Het", the term "heteroaryl" as used herein precisely defines an unsaturated heterocycle for which the double bonds form an aromatic system. Suitable example of heteroaromatic system include: quinoline, indole, pyridine,

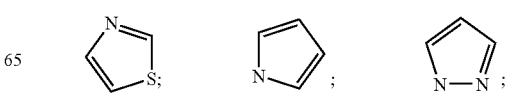

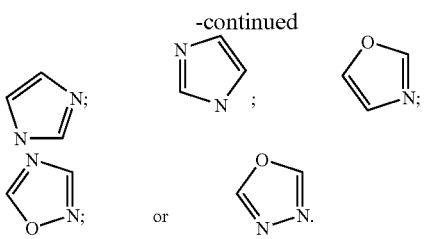

In general, all tautomeric forms and isomeric forms and mixtures, whether individual geometric isomers or optical isomers or racemic or non-racemic mixtures of isomers, of a chemical structure or compound are intended, unless the specific stereochemistry or isomeric form is specifically indicated in the compound name or structure.

The term "pharmaceutically acceptable salt" as used herein includes those derived from pharmaceutically acceptable bases. Examples of suitable bases include choline, ethanolamine and ethylenediamine. $Na^+$, $K^+$, and $Ca^{++}$ salts are also contemplated to be within the scope of the invention (also see Pharmaceutical Salts, Birge, S. M. et al., J. Pharm. Sci., (1977), 66, 1-19, incorporated herein by reference).

The term "pharmaceutically acceptable ester" as used herein, either alone or in combination with another substituent, means esters of the compound of formula I in which any of the carboxyl functions of the molecule, but preferably the carboxy terminus, is replaced by an alkoxycarbonyl function:

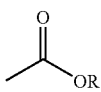

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters are found in Design of Prodrugs, Bundgaard, H. Ed. Elsevier (1985) incorporated herewith by reference. Such pharmaceutically acceptable esters are usually hydrolyzed in vivo when injected in a mammal and transformed into the acid form of the compound of formula I. With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

The following chemicals may be referred to by these abbreviations:

| Abbreviation | Chemical Name |
|---|---|
| ACN | Acetonitrile |
| BOC | Tert-butoxylcarbonyl |
| DABCO | 1,4-diazabicyclo[2.2.2]octane |
| DBU | 1,8-Diazabicyclo[5.4.0]undec-7-ene |
| DCC | 1,3-Dicyclohexylcarbodiimide |
| DCHA | Dicyclohexylamine |
| DCM | Dichloromethane |
| DIPEA or DIEA | Diisopropylethylamine or Hünigs-Base |
| DMAP | Dimethylaminopyridine |
| DMF | N,N-Dimethylformamide |
| DMSO | Dimethylsulfoxide |
| DMTMM | 4-(4,6-Dimethoxy-1,3,5-triazin-2-yl)-4-methylmorpholinium Chloride |
| EDC | 1-(3-dimethylaminopropyl)-3-ethylcarbodiimide hydrocholide |
| HATU | O-(7-azabenzotriazol-1-yl)-N,N,',N'-tetramethyluronium hexafluorophosphate |
| HBTU | O-Benzotriazol-1-yl-N,N,',N'-tetramethyluronium hexafluorophosphate |
| HOAT | 1-Hydroxy-7-azabenzotriazole |
| HOBT | 1-Hydroxybenzotriazole |
| IPA | Isopropyl alcohol |
| KDMO | Potassium 3,7-dimethyl-3-octanoxide |
| MCH | Methylcyclohexane |
| MIBK | 4-Methyl-2-pentanone |
| MTBE | Methyl, tert-butyl ether |
| NMP | 1-Methyl-2-pyrrolidinone |
| SEH | Sodium 2-ethylhexanoate |
| TBTU | O-(Benzotriazol-1-yl)-N,N,N',N'-tetramethyluronium tetrafluoroborate |
| THF | Tetrahydofuran |

EMBODIMENTS OF THE INVENTION

In the synthetic schemes below, unless specified otherwise, all the substituent groups in the chemical formulas shall have the same meanings as in the Formula (I). The reactants used in the synthetic schemes described below may be obtained either as described herein, or if not described herein, are themselves either commercially available or may be prepared from commercially available materials by methods known in the art. Certain starting materials, for example, may be obtained by methods described in the International Patent Applications WO 00/09543, WO 00/09558, WO 00/59929, U.S. Pat. No. 6,323,180 B1 and U.S. Pat. No. 6,608,027 B1.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by High Pressure Liquid Chromatography (HPLC), if desired, and intermediates and products may be purified by chromatography on silica gel and/or by recrystallization.

I. Preparation of QUIN

In one embodiment, the present invention is directed to the following general multi-step synthetic methods for preparing the intermediate compounds of formula QUIN, as well as the individual steps and intermediates set forth therein. Those compounds of formula QUIN wherein X is a halogen are herein designated as formula QUIN-1 and those compounds of formula QUIN wherein X is an $SO_2R$ group, where R is as defined previously, are herein designated as formula QUIN-2. The compounds of formula QUIN-1 and QUIN-2 are prepared as set forth in Schemes IA and IB below, respectively:

SCHEME IA-1 to QUIN-1

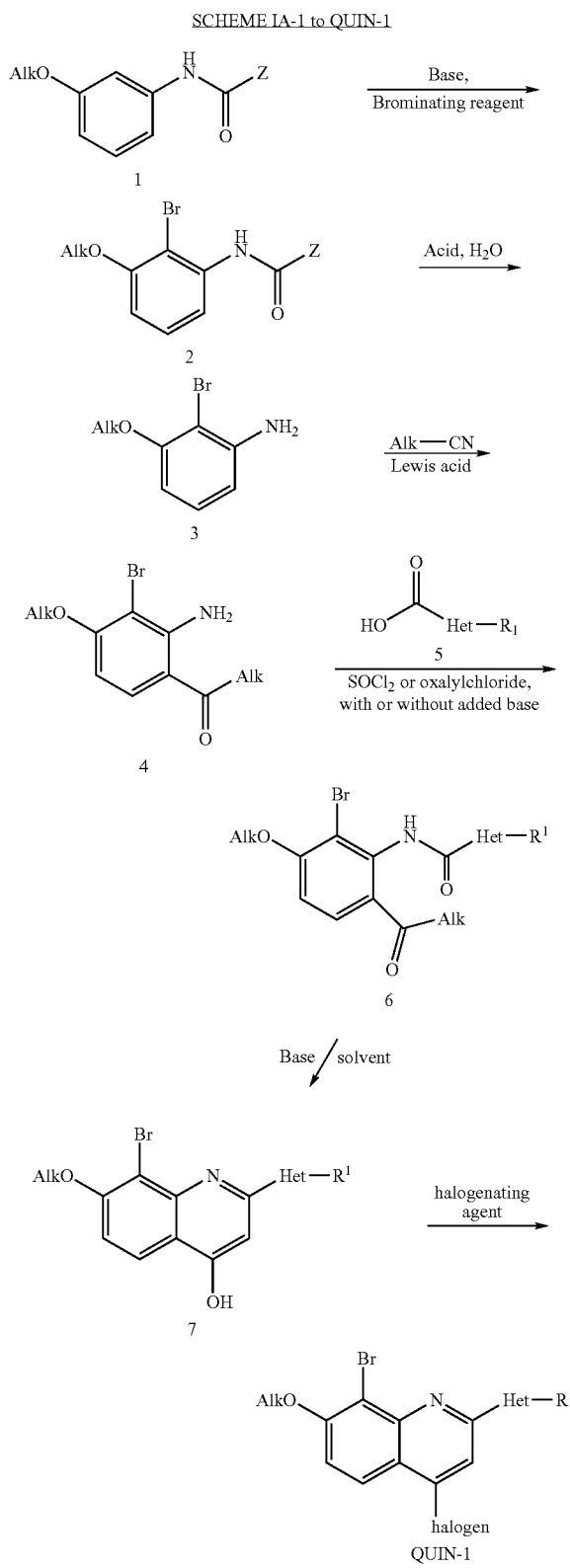

wherein each Alk is independently a $C_1$-$C_6$ alkyl group, X is a halogen atom, Z is tert-butyl or t-butyl-oxy, and $R^1$ and Het in this and subsequent schemes are as defined for Formula I.

In the first step, a compound of formula 1 is treated with a base and a brominating agent to obtain compound 2. The general requirements for this step are the use of a base of strength sufficient to form the desired dianion. This could be any alkyllithium, a metalloamide such as Lithium diisopropylamide (LDA), Lithium tetramethylpiperidide, a metallohexamethyldisilazide such as KHMDS, an organozincate, a metal alkoxide in a cation-solvating solvent such as DMSO, and the like. The preferred bases would be n-Butyllithium and LDA. Any organic solvent that does not interfere with the dianion formation could be used, such as THF, alkyl-THF's, dioxane, alkanes, cycloalkanes, dialkylethers such as MTBE, cyclopentylmethylether, dibutylether, and the like. The preferred solvents would be THF, alkyl-THF's and alkanes. The temperature for the dianion formation could be between −100° C. and 25° C., with the preferred range between −30° C. and 25° C. The brominating reagent could be any compound which contains a labile bromine atom such as $Br_2$, NBS, bromohydantoins, N-bromophthalimides, bromohaloalkanes such as 1,2-dibromotetrachloroethane and perfluoroalkylbromides, and the like. The preferred brominating reagents would be the bromohaloalkanes. Once the dianion has been generated in a suitable solvent, the brominating reagent could be added neat or in solution, or alternatively the dianion could be added to the brominating reagent either neat or in solution. The preferred mode would be to add the dianion slowly to the brominating reagent in solution. The temperature for the bromination could be between −100° C. and 25° C., with the preferred range between −30° C. and 25° C.

In the next step, compound 2 is hydrolyzed by treatment with an aqueous acid mixture to obtain 3. Any aqueous acid mixture could be used such as water with [trifluoroacetic acid, a chloroacetic acid such as trichloroacetic acid, a sulfonic acid such as methanesulfonic acid, hydrochloric acid, sulfuric acid, nitric acid, phosphoric acid, a strong acid resin such as DOWEX 50], and the like. The preferred acids would be hydrochloric acid and sulfuric acid in 2-12 M concentration, preferably at least 6M. Cosolvents that are miscible with water could also be used, such as alcohols like ethanol, isopropanol, or ethers such as DME, diglyme, and the like. The hydrolysis could be carried out between 0° C. and 200° C., with the preferred temperature between 0° C. and 100° C.

In the next step, compound 3 is treated with an alkylated nitrile (Alk-CN) and a Lewis acid to obtain compound 4. For the conversion of 3 to 4, Lewis acids by themselves or in combination, could be used, such as $AlCl_3$, $BCl_3$, $GaCl_3$, $FeCl_3$ and mixtures thereof, and the like. The preferred method would be to use $BCl_3$ with $AlCl_3$. Any solvent which will not be easily acylated could be used such as halocarbons, halobenzenes, alkylbenzenes such as toluene, and alkylnitriles such as acetonitrile, with the preferred solvents being 1,2-dichloroethane, fluorobenzene, chlorobenzene and toluene. The reaction temperature could be between 0° C. and 150° C., preferably between 25° C. and 75° C.

In the next step, compound 4 is acylated with compound 5 to obtain compound 6. For the conversion of 4 to 6, acylation could be achieved by either first converting carboxylic acid 5 to an activated form such as an acid chloride or by using standard peptide coupling protocols. The preferred method would be to create the acid chloride of compound 5 using oxalyl chloride or thionyl chloride. This activated species would then be coupled with aniline 4 in any organic solvent or in water, with or without an added base. The preferred solvents would be NMP and THF and the preferred base (if used) is triethylamine. The reaction temperature could be between −30° C. and 150° C., preferably between −20° C. and 50° C.

In the next step, compound 6 is cyclized in the presence of a base to obtain compound 7. Compound 6 can be isolated and purified, or alternatively, crude 6 in an organic solvent such as NMP can simply be subjected to the cyclization conditions to furnish quinolone 7 directly, preforming two steps in a one-pot process. For the conversion of 6 to 7 in Scheme I, any base capable of forming the enolate could be used, such as t-BuOK, KDMO, LDA, and the like, with t-BuOK and KDMO being preferred. Any organic solvent which does not react with the enolate could be used, such as THF's, dioxane, DMSO, NMP, DME, and the like, with NMP, DME and DMSO being preferred. The cyclization could be performed at any temperature between 25° C. and 150° C., with 50° C. to 100° C. being preferred.

In the final step, hydroxoquinoline compound 7 is treated with a halogenating agent to obtain the compound QUIN. For the conversion of 7 to QUIN in Scheme I, many halogenating reagents could be used, such as methanesulfonyl chloride, $SOCl_2$, $POCl_3$, $PCl_3$, $PCl_5$, $POBr_3$, HF, and the like, with $POCl_3$ and $SOCl_2$ being preferred. The halogenation could be performed neat in the halogenating reagent, or in any organic solvent which does not react with the halogenating reagent, such as DME, diglyme, THF's, halocarbons and the like, with DME and THF's being preferred. The reaction temperature could be between –20° C. and 150° C. with 25° C. to 100° C. being preferred.

THF, toluene and DMF, preferably acetonitrile. The resulting species is then reacted in situ, under acidic conditions (for example in the presence of acetic, trifluoroacetic, hydrochloric acid or the like, preferably acetic acid), with a sulfinate salt $RSO_2M$ wherein M is an alkali metal, such as $PhSO_2Na$, $PhSO_2K$ or $PhSO_2Cs$ at a suitable reaction temperature, for example in the range of 0 to 100° C., preferably 25 to 50° C. The sulfonequinoline product can be isolated from the reaction mixture using conventional techniques well know to those skilled in the art. In one embodiment, the sulfonequinoline can be crystallized out by cooling the solution to room temperature and adding water. The crystallized product can then be filtered, rinsed and washed using conventional techniques.

In particular, the individual intermediate compounds 4, 6, 7, QUIN-1 and QUIN-2, as well as the synthetic procedures to obtain these compounds, all as depicted in the above schemes, are additional aspects and embodiments of the present invention.

I.A. General Embodiment Relating to Quinoline Compounds 7, QUIN-1 and QUIN-2

Another aspect of the present invention are the quinoline intermediates 7, QUIN-1 and QUIN-2 set forth above, as represented by the general formula QUIN' below:

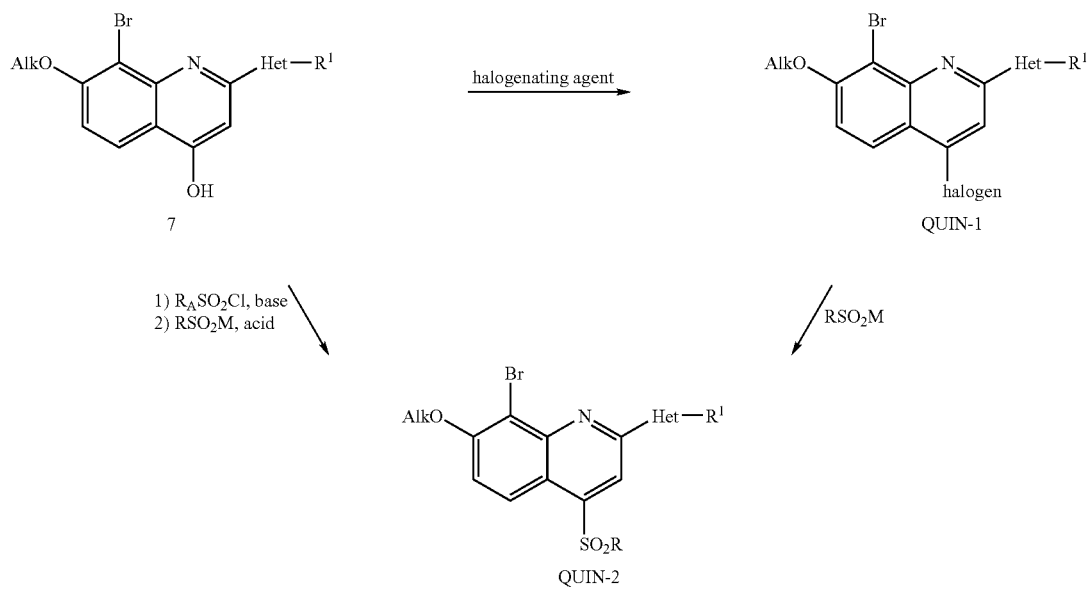

In a first embodiment, the hydroxyl-susbtituted quinolines 7 can first be converted to the halogen substituted quinolines QUIN-1 according the final step of Scheme IA above. The compound of formula QUIN-1 is then converted to the target sulfonequinoline QUIN-2 by reaction with a sulfinate salt $RSO_2M$, wherein R is as defined previously and M is an alkali metal, such as $PhSO_2Na$, $PhSO_2K$ or $PhSO_2Cs$.

Alternatively, compound 7 can be converted to the sulfonequinoline QUIN-2 in a one-pot procedure by first generating an intermediate sulfonate by reaction with an arene sulfonylchloride compound $R_ASO_2Cl$ wherein $R_A$ is an electron rich arene group, such as benzenesulfonyl chloride or tosyl chloride, in the presence of a suitable base in a sutiable solvent. Suitable bases for this step include tertiary amine bases such as N-methylpyrrolidine and diisopropylethylamine, and suitable solvents include aprotic solvents such as acetonitrile, wherein Het is a five-, six- or seven-membered saturated or unsaturated heterocycle containing from one to four heteroatoms selected from nitrogen, oxygen and sulfur; said heterocycle being substituted with $R^1$ at any available position on the heterocycle;

$R^1$ is $R^{20}$, —$NR^{22}COR^{20}$, —$NR^{22}COOR^{20}$—$NR^{22}R^{21}$ and —$NR^{22}CONR^{21}R^{23}$, wherein $R^{20}$ is selected from $(C_{1-8})$alkyl, $(C_{3-7})$cycloalkyl and $(C_{3-7})$cycloalkyl$(C_{1-4})$alkyl-, wherein said cycloalkyl or cycloalkylalkyl may be mono-, di- or tri-substituted with $(C_{1-3})$alkyl;

$R^{21}$ is H or has one of the meanings of $R^{20}$ as defined above, $R^{22}$ and $R^{23}$ are independently selected from H and methyl, Alk is a $C_1$-$C_6$ alkyl group;

and X' is a hydroxyl group, a halogen atom or an $SO_2R$ group, wherein R is $C_{1-6}$alkyl, $C_6$ or $C_{10}$ aryl or heteroaryl.

With respect to the processes for preparing such QUIN' compounds set forth previously, additional embodiments of the present invention include processes comprising:

(a) when X' is a hydroxyl group, cyclizing a compound of formula 6 in the presence of a sutiable base in a suitable solvent to obtain a compound of formula 7:

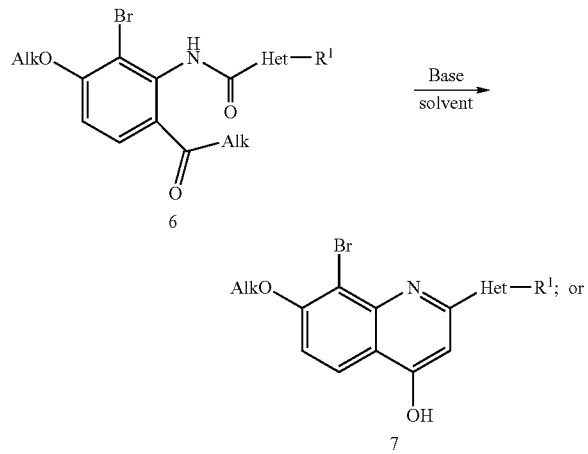

or (b) when X' is a halogen atom, treating a compound of formula 7 with a halogenating agent to obtain a compound of formula QUIN-1:

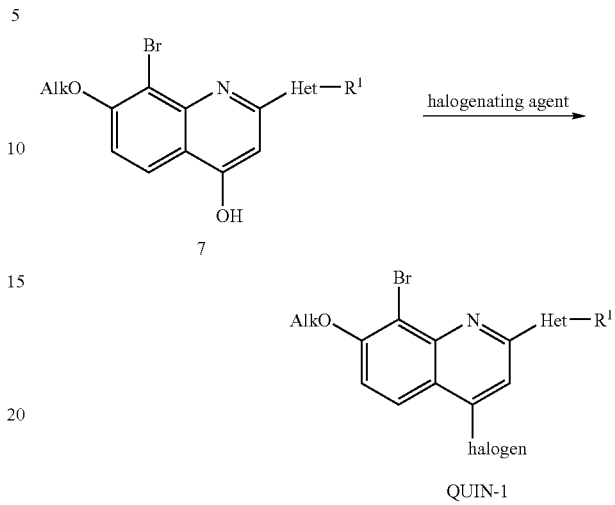

or (c) when X' is an $SO_2R$ group, R is $C_{1-6}$alkyl, $C_6$ or $C_{10}$ aryl or heteroaryl, either:

(1) treating a compound of formula 7 with a halogenating agent to obtain a compound of formula QUIN-1 and then reacting compound QUIN-1 with a sulfinate salt $RSO_2M$, where R is as defined previously and M is an alkali metal, to obtain a compound of formula QUIN-2; or (2) reacting a compound of formula 7 with a compound $R_ASO_2Cl$ wherein $R_A$ is an electron rich arene group, in the presence of a suitable base, and then reacting the resulting compound in situ, under acidic conditions, with a sulfinate salt $RSO_2M$, where R is as defined previously, wherein M is an alkali metal, to obtain a compound of formula QUIN-2:

-continued

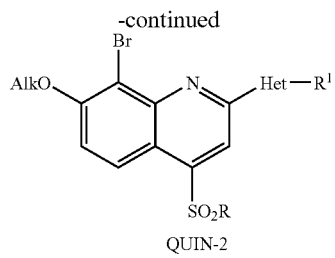

QUIN-2 all of which processes are as set forth previously in Schemes IA and IB above.

II. Preparation of Mono- and Di-peptide QUIN Compounds

In additional embodiments, the present invention is directed to the synthetic methods for preparing of the mono- and di-peptide QUIN compounds P2-QUIN, P3-P2-QUIN and P2-QUIN-P1, as outlined in Schemes II through VI, as well as the individual steps and intermediates in these methods.

SCHEME II - QUIN TO P2-QUIN

QUIN

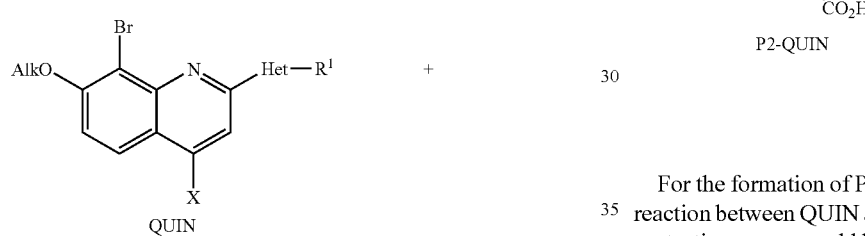

P2-QUIN-PG

-continued

P2-QUIN

For the formation of P2-QUIN-PG in Scheme II, the $S_NAr$ reaction between QUIN and P2-PG, wherein PG is an amino-protecting group, could be performed in any organic solvent, or organic solvent mixture, that will not react with the base used, such as DMSO, DMF, DMA, THF, NMP, DMPU, DME, and the like, or mixtures thereof, with DMSO, DMF, and the combination of DMF and THF being preferred. The reaction could be performed at a temperature between −20° C. and 150° C. with 0° C. to 25° C. being preferred. Any base capable of forming the alkoxide could be used such as t-BuOK, LDA, KHMDS, KDMO, LiTMP, Cs-t-amylate and the like, with t-BuOK, Cs-t-amylate, and KDMO being preferred, and KDMO being most preferred. The preferred amount of base used is 3 to 6 equivalents. Cosolvents such as alkanes and cycloalkanes could also be used, with heptane being a preferred co-solvent.

In the next step, the compound P2-QUIN-PG is deprotected to obtain P2-QUIN under suitable deprotection conditions. For the formation of P2-QUIN, any acid could be used for the removal of PG=BOC, such as TFA, HCl, methanesulfonic acid and the like, with HCl being preferred. For PG=CBZ, any hydrogenative or transfer hydrogenative removal could be used, such as $H_2$ with Pd/C, $NH_4HCO_3$ with Pd/C, or $HCO_2H$ with Pd/C, with $HCO_2H$ with Pd/C being preferred. For PG=FMOC, and organic amine could be used such as $Et_2NH$, morpholine, piperidine, and the like, with morpholine and piperidine being preferred. The product P2-QUIN may be isolated by precipitation from aqueous acid or by standard extractive isolation once the free carboxylic acid has been generated.

SCHEME III - QUIN TO P3-P2-QUIN

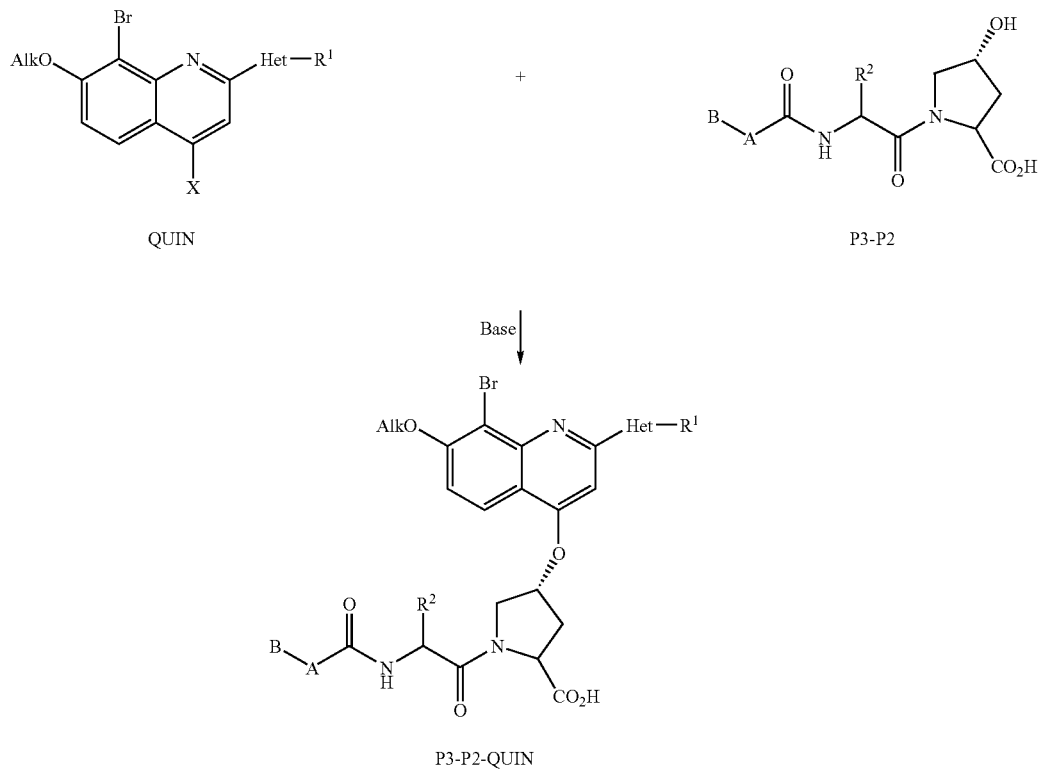

For the formation of P3-P2-QUIN in Scheme III, the $S_NAr$ reaction could be performed in any organic solvent, or organic solvent mixture, that will not react with the base used, such as DMSO, DMF, DMA, THF, NMP, DMPU, DME, and the like, or mixtures thereof, with DMSO, DMF, and the combination of DMF and THF being preferred. The reaction could be performed at a temperature between −20° C. and 150° C. with 0° C. to 25° C. being preferred. Any base capable of forming the alkoxide could be used such as t-BuOK, LDA, KHMDS, KDMO, LiTMP, Cs-t-amylate and the like, with t-BuOK, Cs-t-amylate and KDMO being preferred, and KDMO being most preferred. The preferred amount of base used is 3-6 equivalents. Cosolvents such as alkanes and cycloalkanes could also be used, with heptane being a preferred co-solvent.

SCHEME IV - QUIN TO P2-QUIN-P1

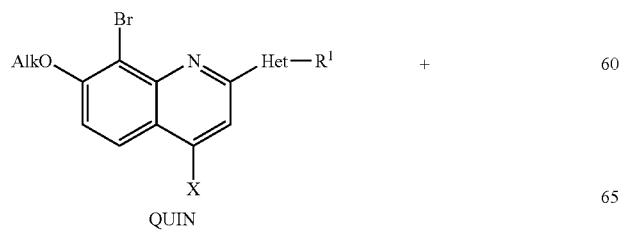

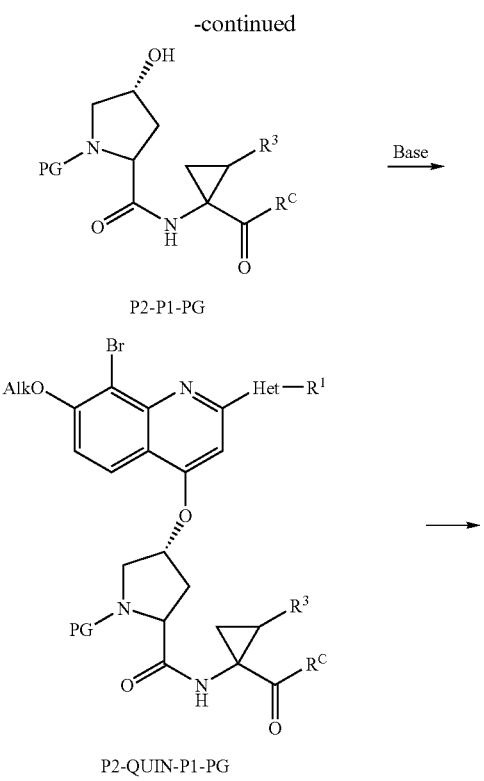

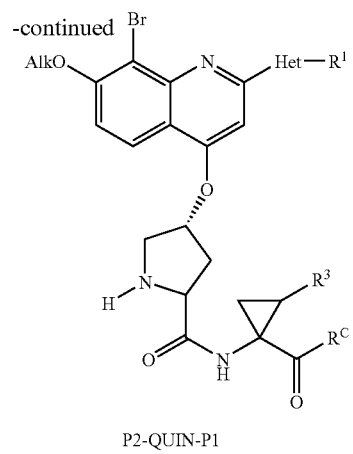

P2-QUIN-P1

For the formation of P2-QUIN-P1-PG in Scheme IV, the S$_N$Ar reaction between QUIN and P2-P1-PG, wherein PG is an amino-protecting group, could be performed in any organic solvent, or organic solvent mixture, that will not react with the base used, such as DMSO, DMF, DMA, THF, NMP, DMPU, DME, and the like, or mixtures thereof, with DMSO, DMF and the combination of DMF and THF being preferred. The reaction could be performed at a temperature between −20° C. and 150° C. with 0° C. to 25° C. being preferred. Any base capable of forming the alkoxide could be used such as t-BuOK, LDA, KHMDS, KDMO, LiTMP, Cs-t-amylate and the like, with t-BuOK, Cs-t-amylate and KDMO being preferred, and KDMO being most preferred. The preferred amount of base used is 3-6 equivalents. Cosolvents such as alkanes and cycloalkanes could also be used, with heptane being a preferred co-solvent.

The removal of the amino-protecting group in the next step to obtain P2-QUIN-P1 is performed under suitable deprotection conditions, for example, treatment with any acid for the removal of PG=BOC, such as TFA, HCl, methanesulfonic acid and the like, with HCl being preferred. For PG=CBZ, any hydrogenative or transfer hydrogenative removal could be used, such as H$_2$ with Pd/C, NH$_4$HCO$_3$ with Pd/C, or HCO$_2$H with Pd/C, with HCO$_2$H with Pd/C being preferred, with the proviso that R$^3$ not equal to vinyl for the use of PG=CBZ. For PG=FMOC, and organic amine could be used such as Et$_2$NH, morpholine, piperidine, and the like, with morpholine and piperidine being preferred.

SCHEME V - P2-QUIN TO P3-P2-QUIN

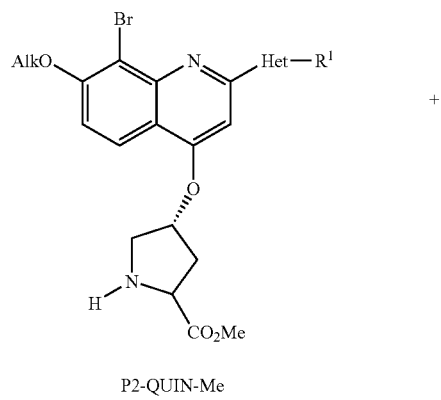

P2-QUIN-Me

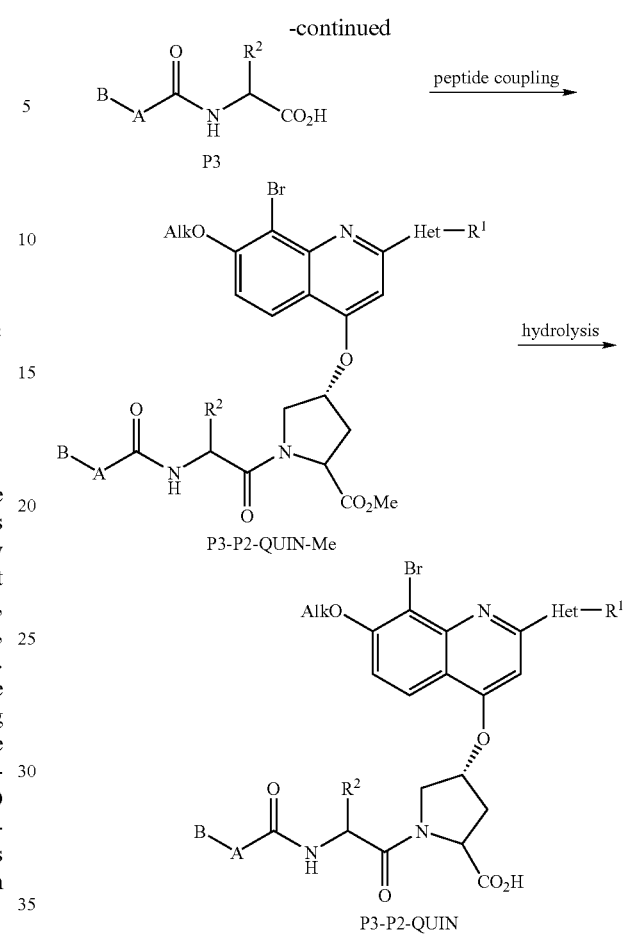

P3-P2-QUIN-Me

P3-P2-QUIN

The peptide coupling between P2-QUIN-Me (obtainable via Scheme II but using the methyl-ester of P2-PG as starting material) and P3 to give P3-P2-QUIN-Me in Scheme V could be performed using any of the conventional peptide coupling reagents and protocols know in the art. Examples of suitable peptide coupling reagents include, but would not be limited to, DCC, EDC, TBTU, HATU, PYBOP, mixed anhydrides, and acidhalides. The preferred reagent would be EDC or mixed anhydrides formed with chloroformates such as isobutylchloroformate or sulfonyl chlorides such as tosylchloride and a tertiary amine such as N-methylpyrrolidine or N-methylmorpholine. The coupling can be performed in any suitable non-reactive organic solvent such as, for example, acetonitrile, THF, CH$_2$Cl$_2$,1,2-dichloroethane, DMA, NMP, DMPU or dioxane. The reaction temperature could be between −78° C. and 100° C., with −30° C. to 25° C. being preferred.

The subsequent hydrolysis to give P3-P2-QUIN in Scheme V could be performed with an aqueous basic solution, optionally containing a co-solvent that is miscible with H$_2$O such as THF, dioxane, alcohols, or DME or combinations of these co-solvents. The preferred solvent mixture would be aqueous base containing THF as a co-solvent. Any water soluble base could be used such as LiOH, NaOH, KOH, Na$_2$CO$_3$, K$_2$CO$_3$, and the like. The preferred base would be LiOH. The amount of base could vary from 1 to 100 equivalents with 1-10 equivalents being preferred. The concentration of base could range from 0.25 M to 12 M, with 1-4 M being preferred. The reaction temperature could vary from −40° C. to 100° C., with −20° C. to 50° C. being preferred.

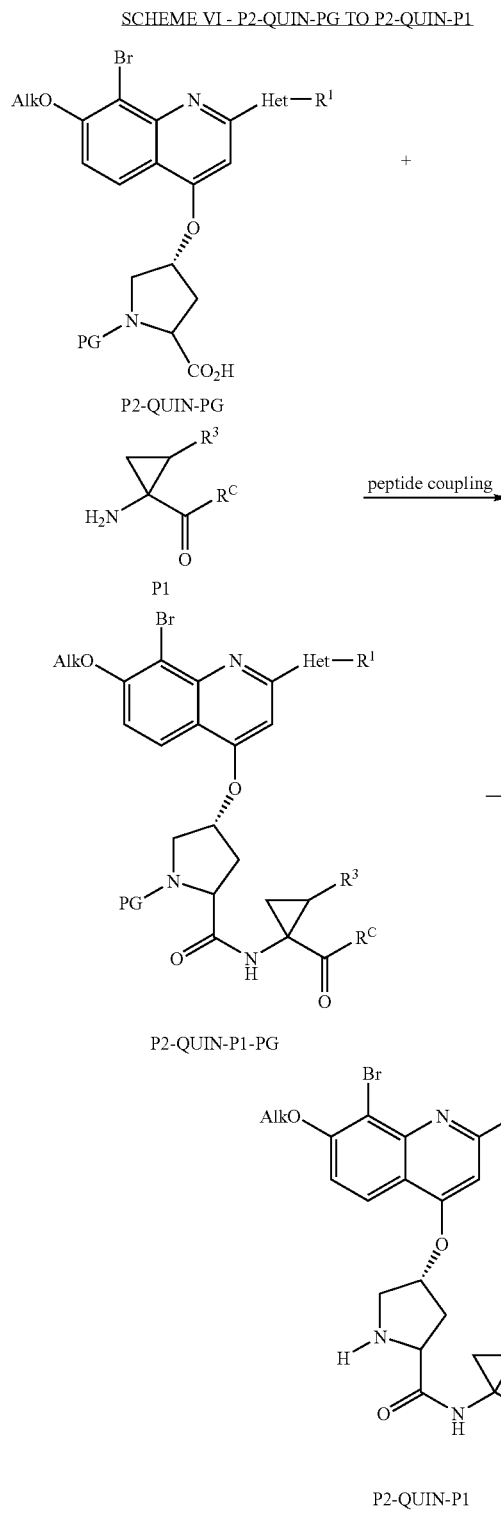

The peptide coupling between P2-QUIN-PG, wherein PG is an amino-protecting group, and P1 to give P2-QUIN-P1-PG in Scheme VI could be performed using any of the conventional peptide coupling reagents and protocols known in the art. Examples of suitable reagents and conditions are outlined above with respect to peptide coupling step of Scheme V.

The removal of the amino-protecting group in the last step of Scheme VI could be performed under the conditions as described above for the deprotection step in Scheme IV.

III. Preparation of Formula I

In additional embodiments, the present invention is directed to the synthetic methods for preparing of the compounds of Formula I, as outlined in Schemes VI through VIII, as well as the individual steps and intermediates in these methods.

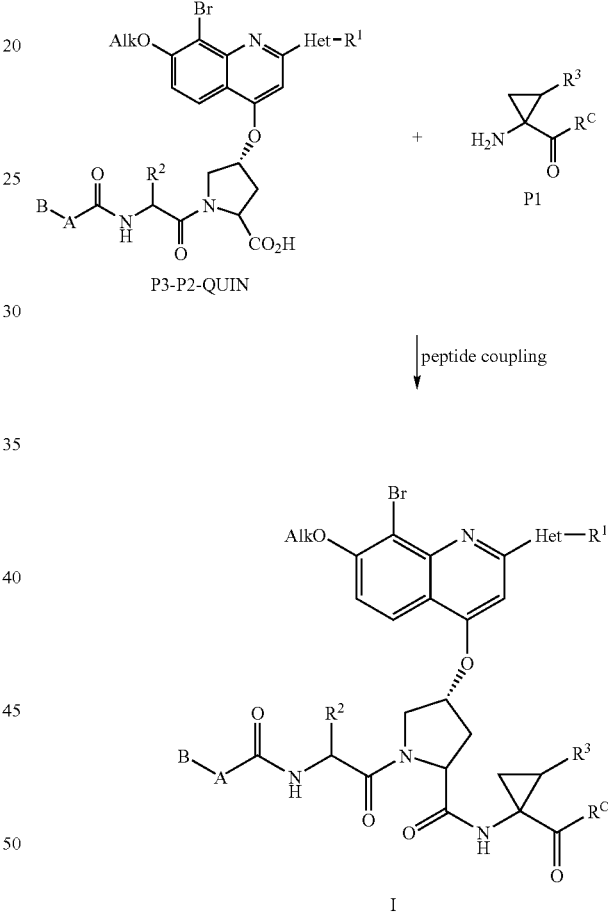

and when $R^C$ is a $C_1$-$C_6$ alkoxy group, optionally subjecting the compound of formula (I) to de-protection conditions to obtain a compound of formula (I) wherein $R^C$ is a hydroxyl group;

and when $R^C$ is a hydroxyl group in the resulting compound of formula (I), optionally coupling this compound with a sulfonamide of formula $R^S SO_2 NH_2$ in the presence of a suitable coupling agent, such as carbodiimide reagents, TBTU or HATU, to obtain a compound of formula (I) wherein $R^C$ is $NHSO_2 R^S$.

The peptide coupling to give compound I in Scheme VII could be performed using any of the conventional peptide coupling reagents and protocols known in the art. Examples of suitable reagents and conditions are outlined above with respect to peptide coupling step of Scheme V.

SCHEME VIII - P2-QUIN-P1 TO FORMULA I

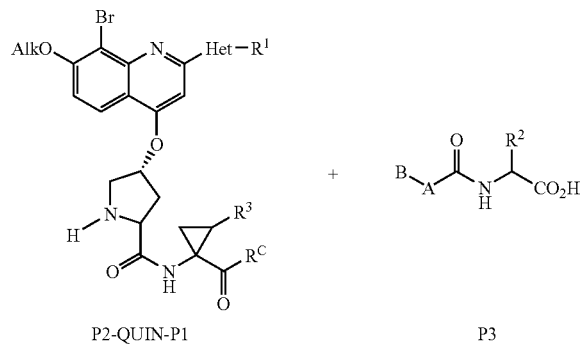

P2-QUIN-P1    P3

| peptide coupling

-continued

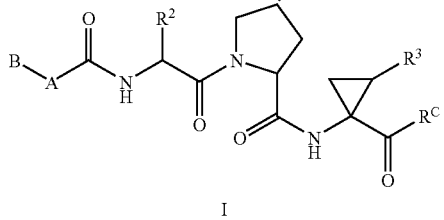

I and when $R^C$ is a $C_1$-$C_6$ alkoxy group, optionally subjecting the compound of formula (I) to de-protection conditions to obtain a compound of formula (I) wherein $R^C$ is a hydroxyl group;

and when $R^C$ is a hydroxyl group in the resulting compound of formula (I), optionally coupling this compound with a sulfonamide of formula $R^SSO_2NH_2$ in the presence of a suitable coupling agent, such as carbodiimide reagents, TBTU or HATU, to obtain a compound of formula (I) wherein $R^C$ is $NHSO_2R^S$.

The peptide coupling to give compound I in Scheme VIII could be performed using any of the conventional peptide coupling reagents and protocols known in the art. Examples of suitable reagents and conditions are outlined above with respect to peptide coupling step of Scheme V.

SCHEME IX - QUIN TO Formula I

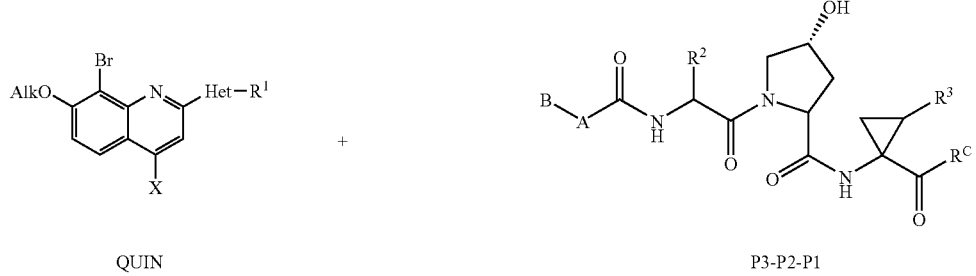

QUIN    P3-P2-P1

Base | $S_NAr$

-continued

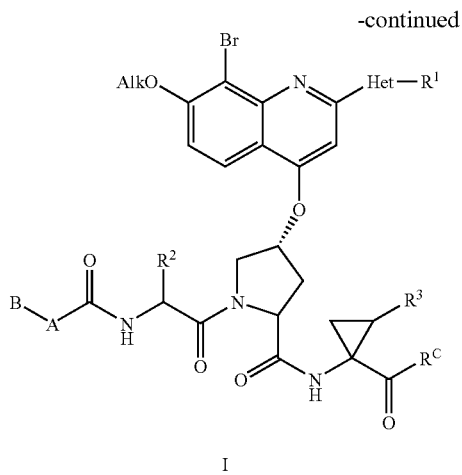

I and when $R^C$ is a $C_1$-$C_6$ alkoxy group, optionally subjecting the compound of formula (I) to de-protection conditions to obtain a compound of formula (I) wherein $R^C$ is a hydroxyl group;

and when $R^C$ is a hydroxyl group in the resulting compound of formula (I), optionally coupling this compound with a sulfonamide of formula $R^SSO_2NH_2$ in the presence of a suitable coupling agent, such as carbodiimide reagents, TBTU or HATU, to obtain a compound of formula (I) wherein $R^C$ is $NHSO_2R^S$.

For the formation of compound I in Scheme IX, the $S_NAr$ reaction could be performed in any organic solvent, or organic solvent mixture, that will not react with the base used, such as DMSO, DMF, DMA, THF, NMP, DMPU, DME, and the like, or mixtures thereof, with DMSO, DMF and the combination of DMF and THF being preferred. The reaction could be performed at a temperature between −20° C. and 150° C. with 0° C. to 25° C. being preferred. Any base capable of forming the alkoxide could be used such as t-BuOK, LDA, KHMDS, KDMO, LiTMP, Cs-t-amylate and the like, with t-BuOK, Cs-t-amylate and KDMO being preferred, and KDMO being most preferred. The preferred amount of base used is 3-6 equivalents. Cosolvents such as alkanes and cycloalkanes could also be used, with heptane being a preferred co-solvent.

III.A. General Embodiments Relating to Schemes II, III, IV and IX

Another aspect of the present invention are the $S_NAr$ processes depicted in Schemes II, III, IV and IX, and depicted generally as a process for preparing a compound of formula II:

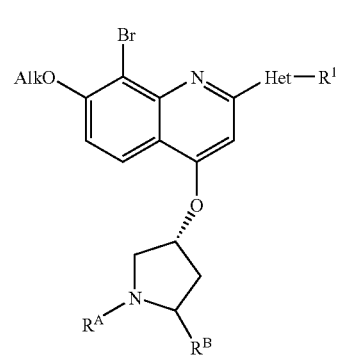

II wherein Het, $R^1$ and Alk are as defined for formula I above;
$R^A$ is PG wherein PG is an amino-protecting group, or $R^A$ is a moiety of the formula:

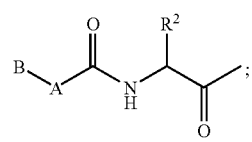

$R^B$ is $CO_2H$ or a moiety of the formula:

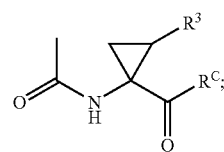

and wherein A, B and $R^2$, $R^3$ and $R^C$ are as defined for formula I above;

said process comprising reacting a compound of formula QUIN, wherein X is a halogen atom or $SO_2R$ group, wherein R is $C_{1-6}$alkyl, $C_6$ or $C_{10}$ aryl or heteroaryl, with a compound of formula P2 to obtain a compound of formula II:

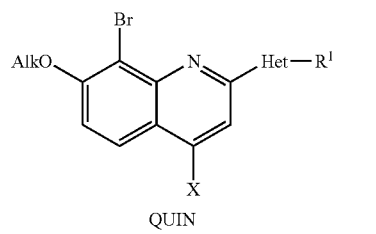

QUIN

+

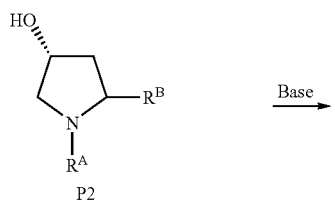

P2

→ Base

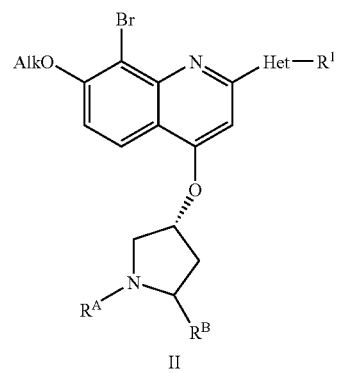

II wherein Alk, Het, $R^1$, $R^A$ and $R^B$ in formulas QUIN and P2 are the same as defined above for formula II.

Another aspect of the present invention are the P2-QUIN and substituted P2-QUIN compounds prepared by the $S_NAr$ processes depicted in Schemes II, III, IV and IX, and as depicted generally by formula II below:

II

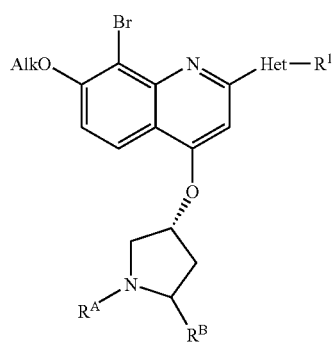

wherein Het, $R^1$ and Alk are as defined for formula I above;

$R^A$ is H or PG wherein PG is an amino-protecting group, or $R^A$ is a moiety of the formula:

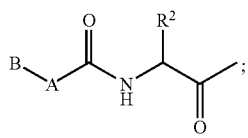

$R^B$ is $CO_2H$ or a moiety of the formula:

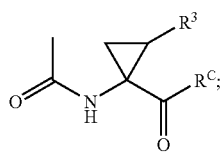

and wherein A, B and $R^2$, $R^3$ and $R^C$ are as defined for formula I above; and wherein when $R^A$ is

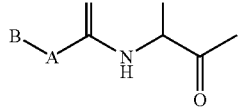

then $R^B$ cannot be

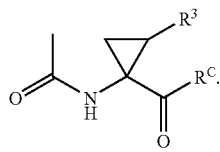

Additional embodiments of formula II above are:
(1) wherein $R^A$ is H or PG and $R^B$ is $CO_2H$; or
(2) wherein $R^A$ is a moiety of the formula:

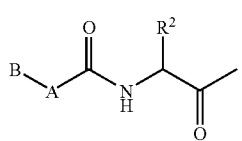

and $R^B$ is $CO_2H$; or
(3) wherein $R^A$ is H or PG and $R^B$ is a moiety of the formula:

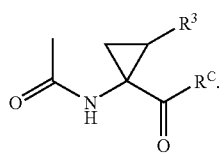

IV. Preparation of Peptidic Starting Materials

The mono-. di- and tripeptidic starting materials employed in the above schemes may be synthesized from known materials using the procedures as outlines in the Schemes X to XIII below.

SCHEME X - PREPARATION OF P3-P2

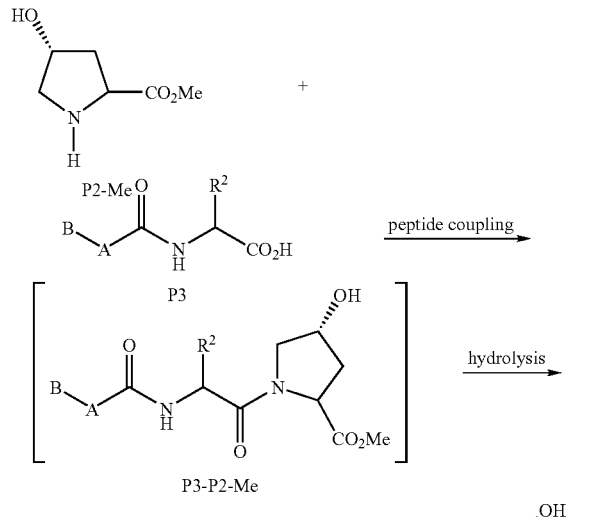

The peptide coupling to give P3-P2-Me in Scheme X could be performed using any of the conventional peptide coupling reagents and protocols known in the art. Examples of suitable reagents and conditions are outlined above with respect to peptide coupling step of Scheme V. The peptide coupling step to give P3-P2-Me in Scheme X is preferably performed in the presence of tosyl chloride and N-methylmorpholine in acetonitrile.

The subsequent hydrolysis to give P3-P2 in Scheme X could be performed without isolation of the P3-P2-Me intermediate using an aqueous basic solution, optionally containing a co-solvent that is miscible with $H_2O$ such as THF, dioxane, alcohols, MeCN, DME or combinations of these co-solvents. The preferred solvent mixture would be aqueous base containing THF as a co-solvent. Any water soluble base could be used such as LiOH, NaOH, KOH, $Na_2CO_3$, $K_2CO_3$, and the like. The preferred base would be LiOH. The amount of base could vary from 1 to 100 equivalents with 1-10 equivalents being preferred. The concentration of base could range from 0.25 M to 12 M, with 1-4 M being preferred. The reaction temperature could vary from $-40°$ C. to $100°$ C., with $-20°$ C. to $50°$ C. being preferred.

SCHEME XI - PREPARATION OF P2-P1

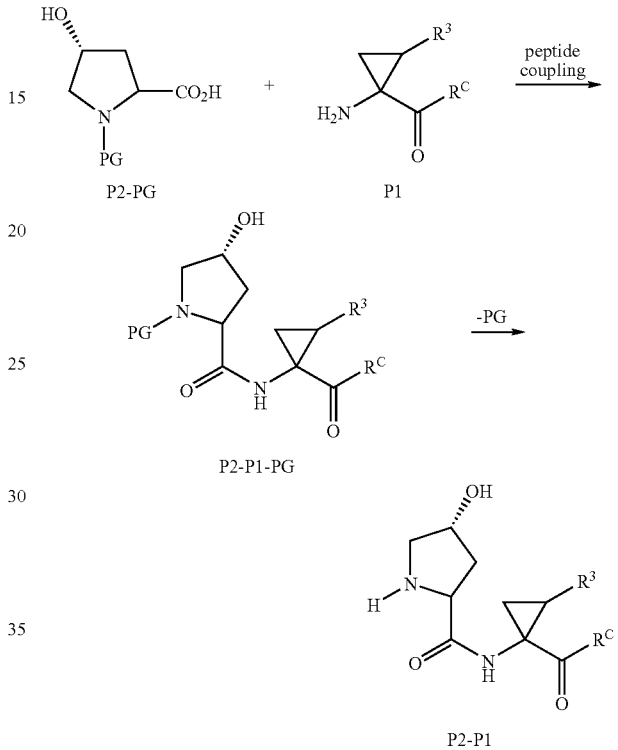

The peptide coupling to give P2-P1-PG, wherein PG is an amino-protecting group, in Scheme XI could be performed using any of the conventional peptide coupling reagents and protocols known in the art. Examples of suitable reagents and conditions are outlined above with respect to peptide coupling step of Scheme V.

The removal of the amino-protecting group in the last step of Scheme XI could be performed under the conditions as described above for the deprotection step in Scheme IV.

SCHEME XII - PREPARATION OF P3-P2-P1

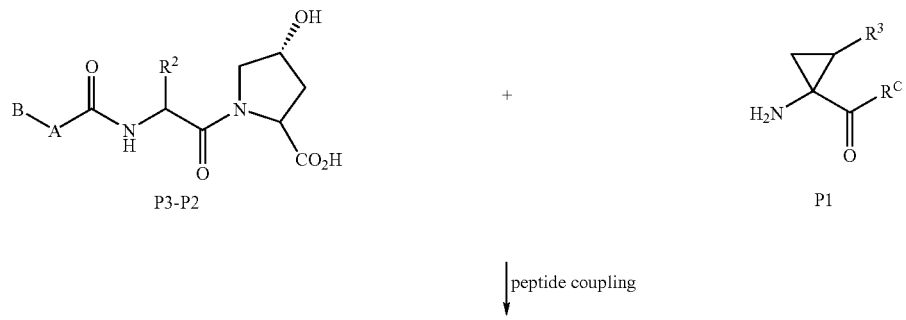

peptide coupling

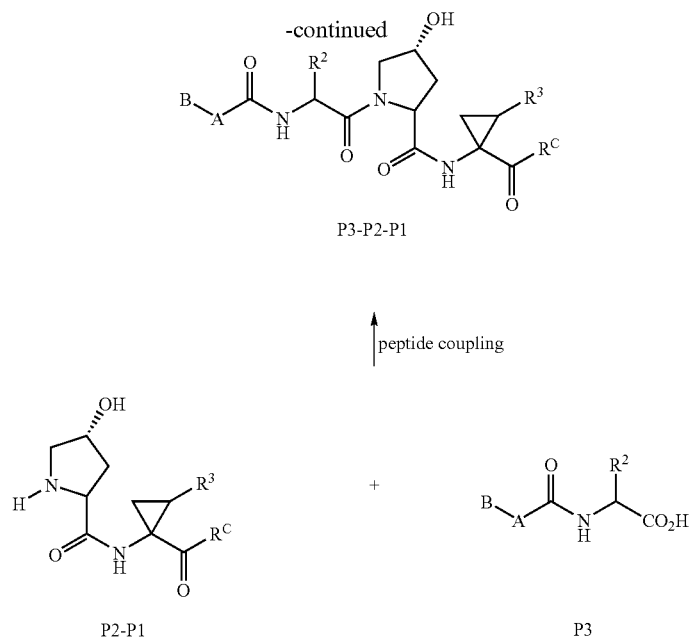

P3-P2-P1

↑ peptide coupling

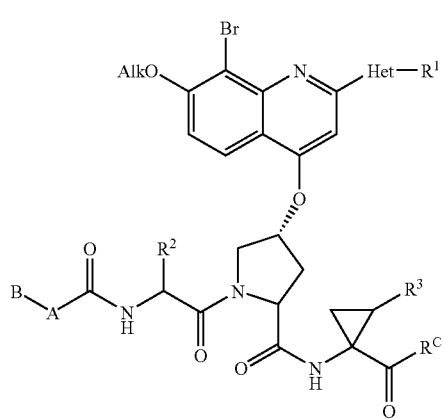

P2-P1 + P3

The peptide couplings to give P3-P2-P1 in Scheme XII could be performed using any of the conventional peptide coupling reagents and protocols known in the art. Examples of suitable reagents and conditions are outlined above with respect to peptide coupling step of Scheme V. When the $R^C$ is an alkoxy group in the P1 moiety of the mono- or dipeptidic starting materials, the resulting tripeptide compound P3-P2-P1 wherein $R^C$ is an alkoxy group may then be subjected to standard hydrolysis conditions to obtain the corresponding tripeptide comound wherein $R^C$ is hydroxyl. Examples of suitable hydrolysis conditions are as outlined above with respect to the hydrolysis step of Scheme X.

Additional embodiments of the invention are directed to the individual steps of the multistep general synthetic method described above and the individual intermediates used in these steps. These individual steps and intermediates of the present invention are described in detail below. All substituent groups are as defined in the general multi-step method above.

V. Preferred Embodiments of the Compound of Formula (I)

The compounds that may be prepared by the processes of the present invention are compounds of the formula (I) as previously set forth, i.e. compound of the following formula:

wherein Het is a five-, six- or seven-membered saturated or unsaturated heterocycle containing from one to four heteroatoms selected from nitrogen, oxygen and sulfur; said heterocycle being substituted with $R^1$ at any available position on the heterocycle;

$R^1$ is $R^{20}$, —$NR^{22}COR^{20}$, —$NR^{22}COOR^{20}$—$NR^{22}R^{21}$ and —$NR^{22}CONR^{21}R^{23}$, wherein $R^{20}$ is selected from $(C_{1-8})$alkyl, $(C_{3-7})$cycloalkyl and $(C_{3-7})$cycloalkyl$(C_{1-4})$alkyl-, wherein said cycloalkyl or cycloalkylalkyl may be mono-, di- or tri-substituted with $(C_{1-3})$alkyl;

$R^{21}$ is H or has one of the meanings of $R^{20}$ as defined above, $R^{22}$ and $R^{23}$ are independently selected from H and methyl, Alk is a $C_1$-$C_6$ alkyl group;

A is O or NH;

B is $(C_{1-10})$alkyl, $(C_{3-7})$cycloalkyl, $(C_{3-7})$cycloalkyl$(C_{1-4})$alkyl,
  a) wherein said cycloalkyl, cycloalkylalkyl may be mono-, di- or tri-substituted with $(C_{1-3})$alkyl; and
  b) wherein said alkyl, cycloalkyl, cycloalkylalkyl may be mono- or di-substituted with substituents selected from hydroxy and $(C_{1-4})$alkoxy; and
  c) wherein all said alkyl-groups may be mono-, di- or tri-substituted with halogen; and
  d) wherein said cycloalkyl-groups being 4-, 5-, 6- or 7-membered having optionally one (for the 4-, 5, 6, or 7-membered) or two (for the 5-, 6- or 7-membered) —$CH_2$-groups not directly linked to each other replaced by —O— such that the O-atom is linked to the group A via at least two C-atoms;

$R^2$ is $(C_{1-8})$alkyl, $(C_{3-7})$cycloalkyl or $(C_{3-7})$cycloalkyl$(C_{1-3})$alkyl, wherein said cycloalkyl groups may be mono-, di- or tri-substituted with $(C_{1-4})$alkyl;

$R^3$ is ethyl or vinyl;

$R^C$ is hydroxyl, $C_1$-$C_6$ alkoxy or $NHSO_2R^S$ wherein $R^S$ is $(C_{1-6})$alkyl, $(C_{3-7})$cycloalkyl, $(C_{3-7})$cycloalkyl$(C_{1-6})$alkyl, phenyl, naphthyl, pyridinyl, phenyl$(C_{1-4})$alkyl, naphthyl $(C_{1-4})$alkyl or pyridinyl$(C_{1-4})$alkyl; all of which optionally being mono-, di- or tri-substituted with substituents selected from halogen, hydroxy, cyano, $(C_{1-4})$alkyl, $(C_{1-6})$ alkoxy, —CO—NH$_2$, —CO—NH(C$_{1-4}$-alkyl), —CO—N(C$_{1-4}$-alkyl)$_2$, —NH$_2$, —NH(C$_{1-4}$-alkyl) and —N(C$_{1-4}$-alkyl)$_2$; and all of which optionally being monosubstituted with nitro;

or R$^S$ can be further selected from: —NH(C$_{1-6}$alkyl), N(C$_{1-6}$ alkyl)$_2$, -Het,

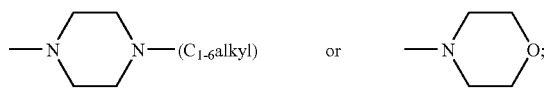

or a pharmaceutically acceptable salt or ester thereof.

In another embodiment of the compounds of formula (I):

Het is selected from the following groups, wherein the arrow desigantes the position of the bond to the quinoline group of formula (I), said heterocycle being substituted with the R$^1$ group at any available position on the heterocycle:

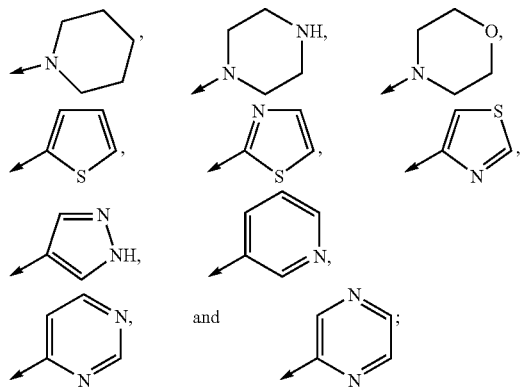

R$^1$ is R$^{20}$, —NHCORO$^{20}$, —NHCOOR$^{20}$, —NHR$^{21}$ and —NHCONR$^{21}$R$^{22}$, wherein R$^{20}$ is selected from (C$_{1-8}$)alkyl, (C$_{3-7}$)cycloalkyl, (C$_{1-3}$)alkyl-(C$_{3-7}$)cycloalkyl, wherein said cycloalkyl, alkyl-cycloalkyl may be mono-, di- or tri-substituted with (C$_{1-3}$)alkyl; and R$^{21}$ is H or has one of the meanings of R$^{20}$ as defined above; and R$^{22}$ is H or methyl;

Alk is a C$_{1-3}$alkyl group;

A is O or NH;

B is (C$_{2-8}$)alkyl, (C$_{3-7}$)cycloalkyl or C$_{1-3}$alkyl-C$_{3-7}$cycloalkyl, all said groups being optionally mono- or di-substituted with methyl or halogen;

R$^2$ is (C$_{1-6}$)alkyl or (C$_{3-7}$)cycloalkyl, both of which being optionally substituted by 1 to 3 substituents selected from C$_{1-4}$ alkyl;

R$^3$ is ethyl or vinyl; and

R$^C$ is hydroxy, NHSO$_2$-methyl, NHSO$_2$-ethyl, NHSO$_2$-(1-methyl)ethyl, NHSO$_2$-propyl, NHSO$_2$-cyclopropyl, NHSO$_2$-cyclopropylmethyl, NHSO$_2$-cyclobutyl, NHSO$_2$-cyclopentyl or NHSO$_2$-phenyl.

In yet another embodiment of formula (I):

Het is selected from the following groups, wherein the arrow desigantes the position of the bond to the quinoline group of formula (I), said heterocycle being substituted with the R$^1$ group at any available position on the heterocycle:

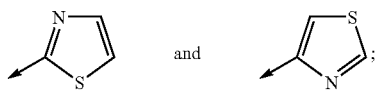

R$^1$ is —NHCOR$^{20}$, —NHCOOR$^{20}$ or —NHR$^{21}$, wherein R$^{20}$ and R$^{21}$ are independently selected from: methyl, ethyl, n-propyl, i-propyl and 2,2-dimethylpropyl;

Alk is a C$_{1-3}$alkyl group;

A is O or NH;

B is selected from: ethyl, n-propyl, cyclopentyl,

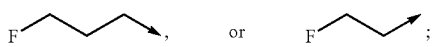

R$^2$ is selected from 1,1-dimethylethyl, cyclopentyl, cyclohexyl and 1-methylcyclohexyl;

R$^3$ is vinyl; and R$^C$ is hydroxy, NHSO$_2$-methyl, NHSO$_2$-cyclopropyl and NHSO$_2$-phenyl.

In yet another embodiment of the compounds of formula (I):

Het-R$^1$ is a group of the formula

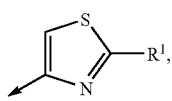

wherein the arrow desigantes the position of the bond to the quinoline group of formula (I);

R$^1$ is —NHCOR$^{20}$, wherein R$^{20}$ is selected from: methyl, ethyl, n-propyl, i-propyl and 2,2-dimethylpropyl;

Alk is a C$_{1-3}$alkyl group;

A is O;

B is selected from: ethyl, n-propyl, 2-fluoroethyl, and cyclopentyl;

R$^2$ is selected from 1,1-dimethylethyl and cyclohexyl; R$^3$ is vinyl; and R$^C$ is hydroxy.

Representative compounds of formula (I) that may be prepared by the processes described herein can be found in Llinas-Brunet et al., U.S. Patent Application Publication No. 2005/0020503 A1, which is herein incorporated by reference in its entirety, including any specific compounds in this publication falling within the scope of formula (I) of the present invention. Representative compounds that may be prepared by the process of the present invention are also listed in the tables below:

TABLE 1

| Cpd. | B | L⁰ | L¹ | R² |
|---|---|---|---|---|
| 1001 | cyclopentyl | MeO— | Br— | —NHC(O)CH₃ |
| 1002 | cyclopentyl | MeO— | Br— | —NHC(O)CH₂-cyclopentyl |
| 1003 | cyclopentyl | MeO— | Br— | —NH-iPr |
| 1004 | cyclopentyl | MeO— | Br— | —NHC(O)CH₂C(CH₃)₃ |
| 1005 | cyclopentyl | MeO— | Br | —NHC(O)CH₂CH₃ |
| 1006 | cyclopentyl | MeO— | Br | —NHC(O)O-iPr |
| 1007 | cyclopentyl | MeO— | Br | —NHC(O)OCH₃ |
| 1008 | cyclopentyl | MeO— | Br | —NHC(O)CH(CH₃)₂ |

TABLE 1-continued

| Cpd. | B | L⁰ | L¹ | R² |
|---|---|---|---|---|
| 1009 | cyclopentylmethyl | MeO— | Br | —NHC(O)CH₂CH₂CH₃ |
| 1010 | CH₂CH₂CH₂CF₃ | MeO— | Br | —NHC(O)CH₂CH₃ |
| 1011 | cyclobutylmethyl | MeO— | Br | —NHC(O)CH₂CH₃ |
| 1012 | isopropyl | MeO— | Br | —NHC(O)CH₂CH₃ |
| 1013 | isobutyl | MeO— | Br | —NHC(O)CH₂CH₃ |
| 1014 | (4-methyl-1,3-dioxan-4-yl)methyl | MeO— | Br | —NHC(O)CH₂-cyclopentyl |
| 1015 | CH(CH₃)CH₂CF₃ | MeO— | Br | —NHC(O)CH₂-cyclopentyl |
| 1016 | sec-butyl | MeO— | Br | —NHC(O)CH₂-cyclopentyl |

TABLE 1-continued

| Cpd. | B | L⁰ | L¹ | R² |
|---|---|---|---|---|
| 1017 | isobutyl | MeO— | Br | -NHC(O)CH₂-cyclopentyl |
| 1018 | (1,3-dioxan-5-yl)methyl | MeO— | Br | -NHC(O)O-iPr |
| 1019 | CF₃-propyl | MeO— | Br | -NHC(O)O-iPr |
| 1020 | bicyclo[2.1.1]pentyl-methyl | MeO— | Br | -NHC(O)O-iPr |
| 1021 | n-propyl | MeO— | Br | -NHC(O)O-iPr |
| 1022 | isobutyl | MeO— | Br | -NHC(O)O-iPr |
| 1023 | (1,3-dioxan-5-yl)methyl | MeO— | Br | -NH-iPr |
| 1024 | bicyclo[2.1.1]pentyl-methyl | MeO— | Br | -NH-iPr |
| 1025 | n-propyl | MeO— | Br | -NH-iPr |
| 1026 | isobutyl | MeO | Br | -NH-iPr |
| 1027 | (1,3-dioxan-5-yl)methyl | MeO | Br | -NHC(O)Et |
| 1028 | cyclopentyl | EtO— | Br | -NHC(O)Et |
| 1029 | cyclopentyl | EtO— | Br | -NHC(O)-iPr |
| 1030 | cyclopentyl | EtO— | Br | -NH-iPr |
| 1031 | cyclopentyl | EtO— | Br | -NHC(O)O-iPr |

TABLE 1-continued

| Cpd. | B | L⁰ | L¹ | R² |
|---|---|---|---|---|
| 1032 | cyclopentylmethyl | PrO— | Br | propionamide |
| 1033 | cyclopentylmethyl | PrO— | Br | isobutyramide |
| 1034 | cyclopentylmethyl | PrO— | Br | isopropylamine |
| 1035 | cyclopentylmethyl | PrO— | Br | isopropyl carbamate |
| 1036 | CF₃-propyl | MeO— | Br | isopropylamine |
| 1037 | F-propyl | MeO— | Br | isopropylamine |
| 1038 | F-butyl | MeO | Br | isopropylamine |
| 1039 | (S)-tetrahydrofuran-3-yl | MeO— | Br | isopropylamine |
| 1040 | butyl | MeO— | Br | isopropylamine |
| 1041 | (S)-3-methylbutan-2-yl | MeO— | Br | isopropylamine |
| 1042 | F-propyl | MeO | Br | propionamide |
| 1043 | F-butyl | MeO | Br | propionamide |
| 1044 | (S)-tetrahydrofuran-3-yl | MeO— | Br | propionamide |
| 1045 | butyl | MeO | Br | propionamide |
| 1046 | 3-methylbutan-2-yl | MeO | Br | propionamide |
| 1047 | F-propyl | MeO | Br | isopropyl carbamate |
| 1048 | F-butyl | MeO | Br | isopropyl carbamate |

TABLE 1-continued

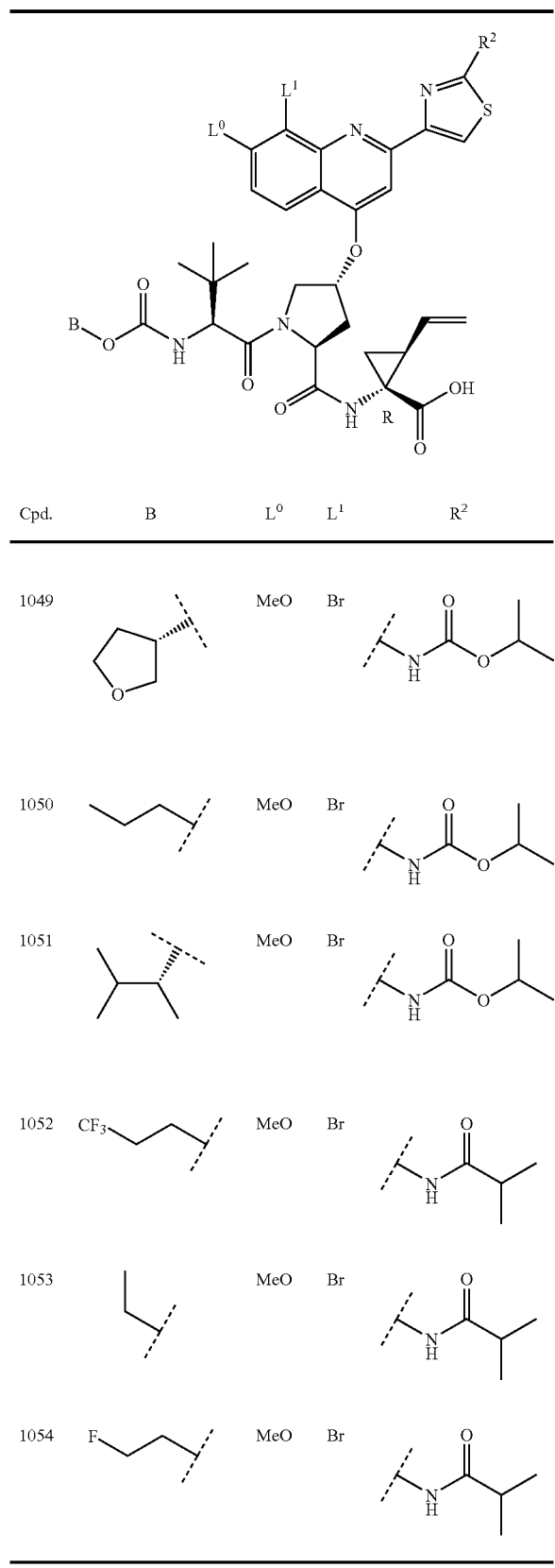

| Cpd. | B | L⁰ | L¹ | R² |
|---|---|---|---|---|
| 1049 | (3-tetrahydrofuranyl) | MeO | Br | isopropyl carbamate |
| 1050 | n-propyl | MeO | Br | isopropyl carbamate |
| 1051 | 2,3-dimethylbutyl | MeO | Br | isopropyl carbamate |
| 1052 | CF₃-CH₂-CH₂- | MeO | Br | isobutyramide |
| 1053 | isobutyl | MeO | Br | isobutyramide |
| 1054 | F-CH₂-CH₂-CH₂- | MeO | Br | isobutyramide |

TABLE 2

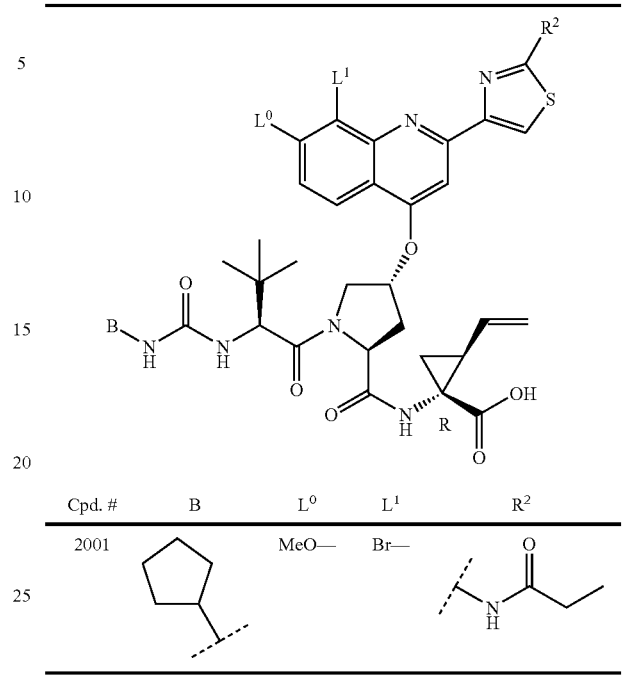

| Cpd. # | B | L⁰ | L¹ | R² |
|---|---|---|---|---|
| 2001 | cyclopentylmethyl | MeO— | Br— | 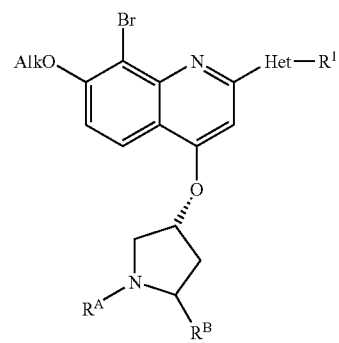 |

The invention claimed is:

1. A process for preparing a compound of formula II:

$$\text{II}$$

(structure shown: AlkO— and Br-substituted quinoline with Het—R¹ and pyrrolidine bearing R^A and R^B)

wherein Het is a five-, six- or seven-membered saturated or unsaturated heterocycle containing from one to four heteroatoms selected from nitrogen, oxygen and sulfur; said heterocycle being substituted with R¹ at any available position on the heterocycle;

R¹ is R²⁰, —NR²²COR²⁰, —NR²²COOR²⁰ —NR²²R²¹ and —NR²²CONR²¹R²³, wherein

R²⁰ is selected from $(C_{1-8})$alkyl, $(C_{3-7})$cycloalkyl and $(C_{3-7})$cycloalkyl$(C_{1-4})$alkyl-, wherein said cycloalkyl or cycloalkylalkyl may be mono-, di- or tri-substituted with $(C_{1-3})$alkyl;

R²¹ is H or has one of the meanings of R²⁰ as defined above,

R²² and R²³ are independently selected from H and methyl,

Alk is a $C_1$-$C_6$ alkyl group;

R^A is PG wherein PG is an amino-protecting group, or R^A is a moiety of the formula:

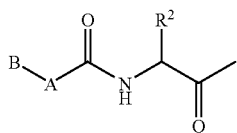

wherein:
A is O or NH;
B is $(C_{1-10})$alkyl, $(C_{3-7})$cycloalkyl, $(C_{3-7})$cycloalkyl$(C_{1-4})$alkyl,
a) wherein said cycloalkyl, cycloalkylalkyl may be mono-, di- or tri-substituted with $(C_1-C_3)$alkyl; and
b) wherein said alkyl, cycloalkyl, cycloalkylalkyl may be mono- or di-substituted with substituents selected from hydroxy and $(C_{1-4})$alkoxy; and
c) wherein all said alkyl-groups may be mono-, di- or tri-substituted with halogen; and
d) wherein said cycloalkyl-groups being 4-, 5-, 6- or 7-membered having optionally one (for the 4-, 5, 6, or 7-membered) or two (for the 5-, 6- or 7-membered) —CH$_2$-groups not directly linked to each other replaced by —O— such that the O-atom is linked to the group A via at least two C-atoms; and
$R^2$ is $(C_{1-8})$alkyl, $(C_{3-7})$cycloalkyl or $(C_{3-7})$cycloalkyl$(C_{1-3})$alkyl, wherein said cycloalkyl groups may be mono-, di- or tri-substituted with $(C_{1-4})$alkyl;
$R^B$ is CO$_2$H or a moiety of the formula:

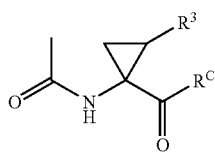

wherein:
$R^3$ is ethyl or vinyl; and
$R^C$ is hydroxyl, $C_1-C_6$ alkoxy or NHSO$_2R^S$ wherein $R^S$ is $(C_{1-6})$alkyl, $(C_{3-7})$cycloalkyl, $(C_{3-7})$cycloalkyl$(C_{1-6})$alkyl, phenyl, naphthyl, pyridinyl, phenyl$(C_{1-4})$alkyl, naphthyl$(C_{1-4})$alkyl or pyridinyl$(C_{1-4})$alkyl; all of which optionally being mono-, di- or tri-substituted with substituents selected from halogen, hydroxy, cyano, $(C_{1-4})$alkyl, $(C_{1-6})$alkoxy, —CO—NH$_2$, —CO—NH(C$_{1-4}$-alkyl), —CO—N(C$_{1-4}$-alkyl)$_2$, —NH$_2$, —NH(C$_{1-4}$-alkyl) and —N(C$_{1-4}$-alkyl)$_2$; and all of which optionally being monosubstituted with nitro;
or $R^S$ can be further selected from: —NH(C$_{1-6}$alkyl), N(C$_{1-6}$ alkyl)$_2$, -Het,

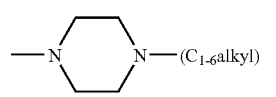 or 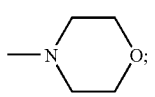

said process comprising reacting a compound of formula QUIN, wherein X is an SO$_2$R group, wherein R is C$_{1-6}$alkyl, C$_6$ or C$_{10}$ aryl or heteroaryl, with a compound of formula P2 to obtain a compound of formula II:

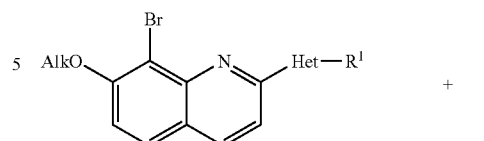

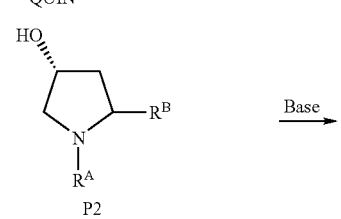

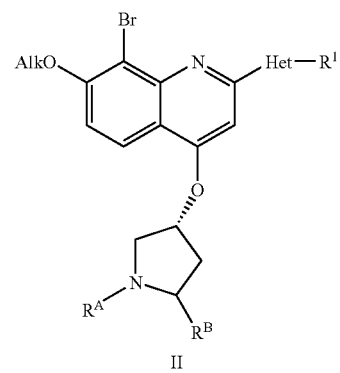

wherein Alk, Het, $R^1$, $R^A$ and $R^B$ in formulas QUIN and P2 are the same as defined above for formula II.

2. A process according to claim 1, wherein $R^A$ is PG and $R^B$ is CO$_2$H.

3. A process according to claim 1, wherein $R^A$ is a moiety of the formula:

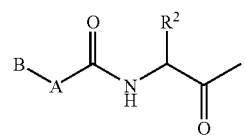

and $R^B$ is CO$_2$H.

4. A process according to claim 1, wherein $R^A$ is PG and $R^B$ is a moiety of the formula:

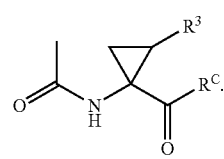

5. A process according to claim 1, wherein $R^A$ is a moiety of the formula:

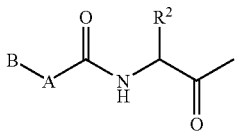

and $R^B$ is a moiety of the formula:

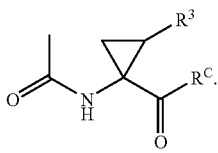

6. A compound of formula II:

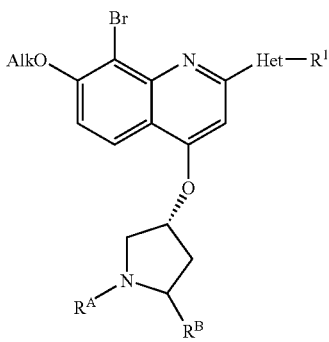

II wherein Het is a five-, six- or seven-membered saturated or unsaturated heterocycle containing from one to four heteroatoms selected from nitrogen, oxygen and sulfur; said heterocycle being substituted with $R^1$ at any available position on the heterocycle;

$R^1$ is $R^{20}$, —$NR^{22}COR^{20}$, —$NR^{22}COOR^{20}$ —$NR^{22}R^{21}$ and —$NR^{22}CONR^{21}R^{23}$, wherein $R^{20}$ is selected from $(C_{1-8})$alkyl, $(C_{3-7})$cycloalkyl and $(C_{3-7})$cycloalkyl$(C_{1-4})$alkyl-, wherein said cycloalkyl or cycloalkylalkyl may be mono-, di- or tri-substituted with $(C_{1-3})$alkyl;

$R^{21}$ is H or has one of the meanings of $R^{20}$ as defined above, $R^{22}$ and $R^{23}$ are independently selected from H and methyl, Alk is a $C_1$-$C_6$ alkyl group;

$R^A$ is H, or $R^A$ is a moiety of the formula:

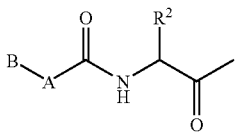

wherein:

A is O or NH;

B is $(C_{1-10})$alkyl, $(C_{3-7})$cycloalkyl, $(C_{3-7})$cycloalkyl$(C_{1-4})$alkyl, a) wherein said cycloalkyl, cycloalkylalkyl may be mono-, di- or tri-substituted with $(C_{1-3})$alkyl; and b) wherein said alkyl, cycloalkyl, cycloalkylalkyl may be mono- or di-substituted with substituents selected from hydroxy and $(C_{1-4})$alkoxy; and c) wherein all said alkyl-groups may be mono-, di- or tri-substituted with halogen; and d) wherein said cycloalkyl-groups being 4-, 5-, 6- or 7-membered having optionally one (for the 4-, 5, 6, or 7-membered) or two (for the 5-, 6- or 7-membered) —$CH_2$-groups not directly linked to each other replaced by —O— such that the O-atom is linked to the group A via at least two C-atoms; and $R^2$ is $(C_{1-8})$alkyl, $(C_{3-7})$cycloalkyl or $(C_{3-7})$cycloalkyl $(C_{1-3})$alkyl, wherein said cycloalkyl groups may be mono-, di- or tri-substituted with $(C_{1-4})$alkyl;

$R^B$ is $CO_2H$.

7. A compound of formula II according to claim 6, wherein $R^A$ is H and $R^B$ is $CO_2H$.

8. A compound of formula II according to claim 6, wherein $R^A$ is a moiety of the formula:

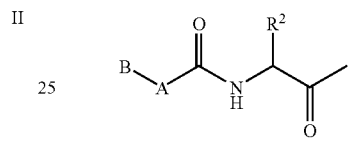

and $R^B$ is $CO_2H$.

9. A compound of the formula QUIN':

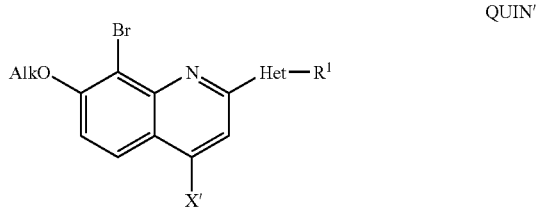

QUIN' wherein Het is a five-, six- or seven-membered saturated or unsaturated heterocycle containing from one to four heteroatoms selected from nitrogen, oxygen and sulfur; said heterocycle being substituted with $R^1$ at any available position on the heterocycle;

$R^1$ is $R^{20}$, —$NR^{22}COR^{20}$, —$NR^{22}COOR^{20}$ —$NR^{22}R^{21}$ and —$NR^{22}CONR^{21}R^{23}$, wherein $R^{20}$ is selected from $(C_{1-8})$alkyl, $(C_{3-7})$cycloalkyl and $(C_{3-7})$cycloalkyl$(C_{1-4})$alkyl-, wherein said cycloalkyl or cycloalkylalkyl may be mono-, di- or tri-substituted with $(C_{1-3})$alkyl;

$R^{21}$ is H or has one of the meanings of $R^{20}$ as defined above, $R^{22}$ and $R^{23}$ are independently selected from H and methyl, Alk is a $C_1$-$C_6$ alkyl group;

and X' is a hydroxyl group; or a halogen atom.

10. A compound of formula QUIN' according to claim 9, wherein X' is a hydroxyl group.

11. A compound of formula QUIN' according to claim 9, wherein X' is a halogen atom.

12. A process for preparing a compound of formula QUIN' according to claim 10, said process comprising:

(a) when X' is a hydroxyl group, cyclizing a compound of formula 6 in the presence of a suitable base in a suitable solvent to obtain a compound of formula 7:

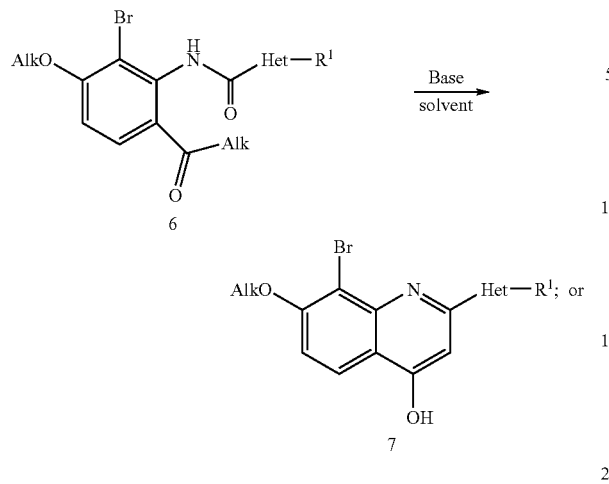
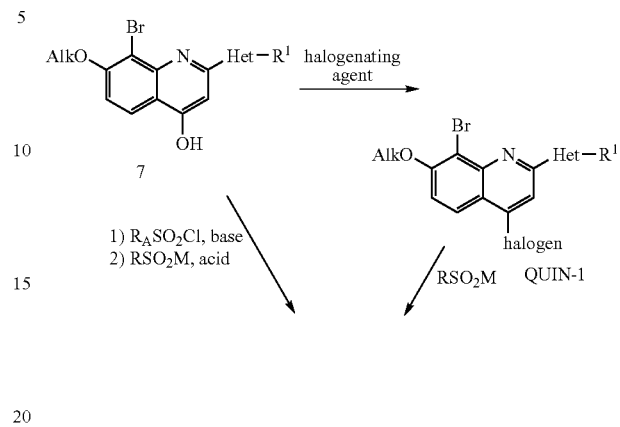
(b) when X' is a halogen atom, treating a compound of formula 7 with a halogenating agent to obtain a compound of formula QUIN-1:
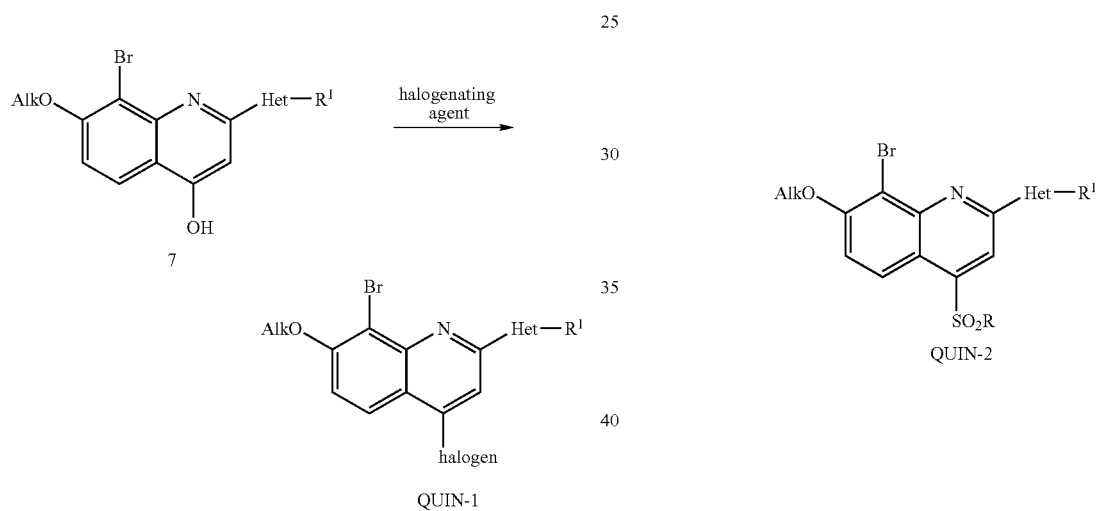

UNITED STATES PATENT AND TRADEMARK OFFICE
CERTIFICATE OF CORRECTION

| | | |
|---|---|---|
| PATENT NO. | : 7,514,557 B2 | Page 1 of 1 |
| APPLICATION NO. | : 11/135533 | |
| DATED | : April 7, 2009 | |
| INVENTOR(S) | : Carl Alan Busacca et al. | |

It is certified that error appears in the above-identified patent and that said Letters Patent is hereby corrected as shown below:

In Column 44, line 64; in the second line of Claim 12, change "10" to --9--.

Delete all of the subject matter appearing at lines 5 through 40 in Column 46.

Signed and Sealed this

Twentieth Day of October, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,514,557 B2 | Page 1 of 1 |
| APPLICATION NO. | : 11/135533 | |
| DATED | : April 7, 2009 | |
| INVENTOR(S) | : Busacca et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 889 days.

Signed and Sealed this

Thirtieth Day of October, 2012

David J. Kappos
*Director of the United States Patent and Trademark Office*